United States Patent
Gross et al.

(10) Patent No.: US 8,129,666 B2
(45) Date of Patent: *Mar. 6, 2012

(54) OPTICAL SURFACE SHAPE DETERMINATION BY MAPPING A LENSLET ARRAY SPOT PATTERN TO SPATIAL FREQUENCY SPACE

(75) Inventors: Erik Gross, Palo Alto, CA (US); Charles Campbell, Berkeley, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/641,011

(22) Filed: Dec. 17, 2009

(65) Prior Publication Data

US 2010/0090090 A1    Apr. 15, 2010

Related U.S. Application Data

(63) Continuation of application No. 11/686,226, filed on Mar. 14, 2007, now Pat. No. 7,652,235.

(60) Provisional application No. 60/782,679, filed on Mar. 14, 2006.

(51) Int. Cl.
*G01J 1/20* (2006.01)
(52) U.S. Cl. .................................................. 250/201.9
(58) Field of Classification Search .............. 250/201.9; 382/280; 356/512; 606/4–6
See application file for complete search history.

(56) References Cited

U.S. PATENT DOCUMENTS

| | | |
|---|---|---|
| 3,993,976 A | 11/1976 | Ginsburg |
| 4,665,913 A | 5/1987 | L'Esperance, Jr. |
| 4,669,466 A | 6/1987 | L'Esperance, Jr. |
| 4,732,148 A | 3/1988 | L'Esperance, Jr. |
| 4,770,172 A | 9/1988 | L'Esperance, Jr. |
| 4,773,414 A | 9/1988 | L'Esperance, Jr. |
| 5,062,702 A | 11/1991 | Bille |
| 5,108,388 A | 4/1992 | Trokel |
| 5,144,630 A | 9/1992 | Lin |

(Continued)

FOREIGN PATENT DOCUMENTS

EP    1 248 093    10/2002

(Continued)

OTHER PUBLICATIONS

Campbell, "The Refractive Group," Optometry & Vision Science. 74(6):381-387, Jun. 1997.

(Continued)

*Primary Examiner* — Thanh X Luu
(74) *Attorney, Agent, or Firm* — AMO Manufacturing USA, LLC

(57) ABSTRACT

Devices systems, and methods can characterize an optical surface of an object. A wavefront sensor system focuses light energy propagating from the object to form a pattern on a detector. The system maps the pattern to an array with a transform function such as a Fourier transform. The values of array correspond to characteristic locations and signals in a transform space, for example an intensity of spatial frequency signals in frequency space. The characteristic location and intensity of these signals in transform space are used to measure the optical surface. For example, a characteristic frequency of a spatial frequency intensity peak in Fourier transform space can be used to estimate the location of spots on the detector. Alternatively, the characteristics can be used to the measure sphere, cylinder and axis of a wavefront, wavefront elevation maps and point spread functions, often without locating positions of individual spots on the detector.

9 Claims, 15 Drawing Sheets

U.S. PATENT DOCUMENTS

| | | | |
|---|---|---|---|
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,339,121 A | 8/1994 | Shimmick et al. |
| 5,520,679 A | 5/1996 | Lin |
| 5,646,791 A | 7/1997 | Glockler |
| 5,742,626 A | 4/1998 | Mead et al. |
| 5,782,822 A | 7/1998 | Telfair et al. |
| 5,912,731 A | 6/1999 | DeLong et al. |
| 5,936,720 A | 8/1999 | Neal et al. |
| 6,004,313 A | 12/1999 | Shimmick et al. |
| 6,052,180 A | 4/2000 | Neal et al. |
| 6,090,102 A | 7/2000 | Telfair et al. |
| 6,095,651 A | 8/2000 | Williams et al. |
| 6,184,974 B1 | 2/2001 | Neal et al. |
| 6,271,915 B1 | 8/2001 | Frey et al. |
| 6,299,311 B1 | 10/2001 | Williams et al. |
| 6,631,991 B2 | 10/2003 | Wirth |
| 6,659,613 B2 | 12/2003 | Applegate et al. |
| 6,750,957 B1 | 6/2004 | Levecq et al. |
| 6,932,475 B2 | 8/2005 | Molebny et al. |
| 7,008,415 B2 | 3/2006 | Yee et al. |
| 7,168,807 B2 | 1/2007 | Chernyak et al. |
| 7,652,235 B2 | 1/2010 | Gross et al. |
| 2003/0151721 A1 | 8/2003 | Lai et al. |
| 2005/0007603 A1 | 1/2005 | Arieli et al. |
| 2005/0012898 A1 | 1/2005 | Chernyak et al. |
| 2006/0017883 A1 | 1/2006 | Dai et al. |
| 2006/0044510 A1 | 3/2006 | Williams et al. |
| 2006/0077398 A1* | 4/2006 | Cantin et al. ............ 356/512 |

FOREIGN PATENT DOCUMENTS

| | | |
|---|---|---|
| EP | 1 324 015 | 7/2003 |
| EP | 1 334 691 | 8/2003 |
| WO | WO 2005/052538 | 6/2005 |

OTHER PUBLICATIONS

Papoulis, Chapter 4: Fourier Series and Sampling Expansions, Systems and Transforms with Applications in Optics, (McGraw-Hill, New York), 1968, p. 116-139.

* cited by examiner

OPTICAL SURFACE SHAPE DETERMINATION BY MAPPING A LENSLET ARRAY SPOT PATTERN TO SPATIAL FREQUENCY SPACE

CROSS-REFERENCES TO RELATED APPLICATIONS

The present application is a Continuation of U.S. Ser. No. 11/686,226 filed Mar. 14, 2007, which application claims the benefit of Provisional Application No. 60/782,679 filed Mar. 14, 2006; the full disclosures, each of which are incorporated herein by reference in their entirety.

BACKGROUND OF THE INVENTION

The present invention is generally related to measurements of optical systems and surfaces. The invention provides devices, systems, and methods for measurement of optical errors of optical systems, and is particularly well-suited for determining a refractive correction of optical errors of the eye. The invention is also particularly well suited to the measurement of optical surfaces such as lenses, spectacles and contacts, including lenses ablated during calibration of a laser eye surgery system.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye. By customizing an ablation pattern based on wavefront measurements and providing improved laser system calibration, it may be possible to correct minor refractive errors so as to reliably and repeatably provide visual acuities greater than 20/20.

Known methods for calculation of a customized ablation pattern using wavefront sensor data generally involves mathematically modeling an optical surface of the eye using expansion series techniques. More specifically, Zernike polynomial series and Fourier series have each been employed to model the optical surface. For example, U.S. patent application Ser. No. 10/872,107, filed on Jun. 17, 2004, and entitled "Iterative Fourier Reconstruction for Laser Surgery and Other Optical Applications", the full disclosure of which is incorporated herein by reference, describes application of a Fourier transform algorithm to measured gradients to reconstruct an optical surface. Coefficients of the Zernike or Fourier series are derived through known fitting techniques, and the refractive correction procedure is then determined using the shape of the optical tissue surface the eye indicated by the mathematical series expansion model.

Work in connection with the present invention suggests that the known methodology for calculation of an optical surface and a laser ablation treatment protocol based on wavefront sensor data may be less than ideal. The known methods which determine a gradient field from several beams of light can be sensitive to errors and "noise" which can arise while finding a location of a light beam, which can lead to a less than ideal refractive correction. Furthermore, the known surface modeling techniques based on gradients can be somewhat indirect, and may lead to unnecessary calculations.

In light of the above, it would be desirable to provide improved optical measurement techniques, particularly for use in measurements of the eye for refractive correction purposes.

BRIEF SUMMARY OF THE INVENTION

The present invention generally provides improved devices, systems, and methods for measuring and/or characterizing optical surfaces. Exemplary embodiments provide systems and methods for measuring and characterizing an optical surface of an object, such as an eye, plastic, ablated plastic, lens, spectacle or contact lens. The system often focuses and/or images light energy propagating from the object to form a pattern on a detector. The system maps the pattern with a transform function to a transform array, with the values of the array corresponding to characteristics, or signals in a transform space. For example, the pattern can be mapped to frequency space with a Fourier transform function and an intensity of spatial frequency signals stored in the array. The location and intensity of these characteristic signals along dimensions in transform space can be used to measure and/or characterize the optical surface. For example, a characteristic frequency of a signal (such as a spatial frequency intensity peak) in Fourier transform space can be used to estimate the location of spots in a Shack-Hartmann wavefront sensor. This estimate can facilitate a search for the location of individual spots to construct a gradient vector field and calculation of a wavefront map using the vector field. In some embodiments, the characteristic frequency signals can be used to the calculate sphere, cylinder and axis of a wavefront, wavefront elevation maps and/or point spread functions, often without locating the positions of individual spots of light. This latter approach may even be more direct and more accurate than approaches which locate the positions of individual spots of light to generate a gradient vector field and then calculate the wavefront map from the vector field.

In a first aspect, the invention provides a method of determining optical characteristics of an object. A lenslet array forms a sport pattern on a detector by focusing light energy propagating from the object. By determining a spatial frequency of light spots in the pattern, locations of the light spots on the detector can be estimated. Using the estimated locations of the light spots in the pattern, the actual locations of the light spots can be identified. The optical characteristics of the object can be calculated using the identified locations.

In many embodiments, the pattern is mapped to a spatial frequency array. The array can have values corresponding to intensities of spatial frequencies in the pattern. A spatial frequency intensity peak can be used to determine the characteristic spatial frequency. The characteristic frequency can be determined from the spatial frequency intensity peak by calculating a centroid of the spatial frequency intensity peak, and the centroid of the peak can correspond to the characteristic spatial frequency. A fast Fourier transform of the pattern can calculate and map the pattern to frequency space. A map of the pattern can be centered in frequency space.

Many embodiments use two dimensional mapping. For example, a two dimensional spatial frequency map can be centered by swapping quadrants of the spatial frequency map. A second spatial frequency corresponding to a second spatial frequency intensity peak can be determined from the array. Estimated locations of the spots along a first dimension can correspond to the first spatial frequency, and estimated locations of the spots along a second dimension can correspond to the second spatial frequency.

In some embodiments, a laser system is calibrated. An object can be ablated with the laser system to form the optical surface on the object. The optical surface can be determined with calculations using frequency information from the pattern. The laser system can be adjusted in response to the optical surface determined.

In another aspect, the invention provides a method for measuring an optical surface, optionally without determining the location of individual spots. Light energy propagating from the object can be focused onto the detector to form a light energy pattern. The pattern can be mapped to a transform array by transforming the pattern with a transform function. A characteristic, often a signal or signal frequency, can be identified from the transform array. The characteristic can correspond to the optical surface of the object. The pattern can be formed by passing the light energy through several lenslets of a lenslet array. The pattern can include several spots of light energy so that the transform map includes several spots of light energy from the pattern. By multiplying a first value from the transform function by second value from the pattern for several values of the function and several values of the pattern, the pattern can be transformed to a map in transform space. The second value can correspond to an intensity of the light energy in the pattern. By mapping the pattern to transform space, the array can be populated with numbers corresponding to signals having amplitudes at locations in transform space. To identify the characteristic, a location of the signal can be selected in transform space such that the location of the signal in the transform space corresponds characteristic and to the optical surface. A sphere and a cylinder of the optical surface can be determined from the identified characteristic. A wavefront elevation map of the optical surface can be determined from the identified characteristic.

In many embodiments, generally using a two dimensional analysis, the array can have values corresponding to intensities of spatial frequencies in the pattern. The characteristic can correspond to a first spatial frequency, and the first spatial frequency can have a non-zero component along a first dimension. The characteristic frequency can correspond to a first spatial frequency intensity peak. A second spatial frequency can correspond to a second spatial frequency intensity peak. The second spatial frequency can be determined from the peak and can have a non-zero component along a second dimension. The pattern can comprise a two dimensional spatial light intensity distribution pattern. The array can comprise a two dimensional array and can have values corresponding to a first coordinate reference along a first dimension in the transform space and a second coordinate reference along a second dimension in the transform space. The characteristic can correspond to a first coordinate location along the first dimension and a second coordinate location along the second dimension. A second characteristic, in many instances a signal, can be identified from the array. The second characteristic can corresponding to third coordinate reference along the first dimension and a fourth coordinate reference along the second dimension. A sphere and a cylinder of the surface can be determined from the four coordinate references. A wavefront elevation map can be determined from the four coordinate references.

In another aspect the invention provides a system for measuring an optical surface of an object. A detector measures light energy propagating along an optical path. A light focusing structure is disposed between the detector and the object to define the optical path and form a light spot pattern on the detector. A processor is coupled to the detector and configured to determine a spatial frequency of the light spots in the pattern. The processor can also be configured to estimate locations of light spots in the pattern from the frequency, and identify locations of light spots using the estimated locations. The processor can also be configured to calculate the optical surface using the identified locations. In many embodiments, the detector comprises a two dimensional CCD array and the structure comprises a two dimensional lenslet array. The processor can be configured to map the pattern to a spatial frequency array, and the array can have values corresponding to intensities of spatial frequencies in the pattern. The processor can be configured to determine the frequency from a spatial frequency intensity peak. The processor can be configured to calculate a centroid of the spatial frequency intensity peak. The centroid of the peak can correspond to the spatial frequency. The processor can be configured to calculate a fast Fourier transform of the pattern. The processor can be configured to center a frequency map of the pattern in a frequency space. The map can be a two dimensional spatial frequency map and the processor can be configured to swap quadrants of the frequency map to center the map. The processor can be configured to determine a second spatial frequency corresponding to a second spatial frequency intensity peak from the array. The process can be configured to estimate locations of the spots along a first dimension. The locations along the first dimension can correspond to the first frequency. The processor can be further configured to estimate locations of the spots along a second dimension. The locations of the spots along the second dimension can correspond to the second spatial frequency.

In another aspect, the invention provides a system for determining an optical characteristic of an object, an in some instances determines the characteristic without determining a location of individual spots of light energy. The system includes a detector which measures a light energy pattern. A processor is coupled to the detector and configured to map the pattern to a signal in transform space and determine the characteristic from the signal. The characteristic can comprise an optical surface. The object can transmit light energy, and optionally the processor can determine the optical surface without determining a location of a light structure in the pattern.

In another aspect, the invention provides a computer-readable storage medium. The medium has a set of instructions for a computer to determine an optical characteristic of an object. The set of instructions uses an input routine operatively associated with a source of detector data. The set of instructions also uses a run routine which maps the data to an array corresponding to signals in a transform space and determines the optical characteristic of the object from the signals. An output routine provides information determined from the optical characteristic for external use outside the computer.

DETAILED DESCRIPTION OF SPECIFIC EMBODIMENTS

1. Description of System and Methods

Figure 1:
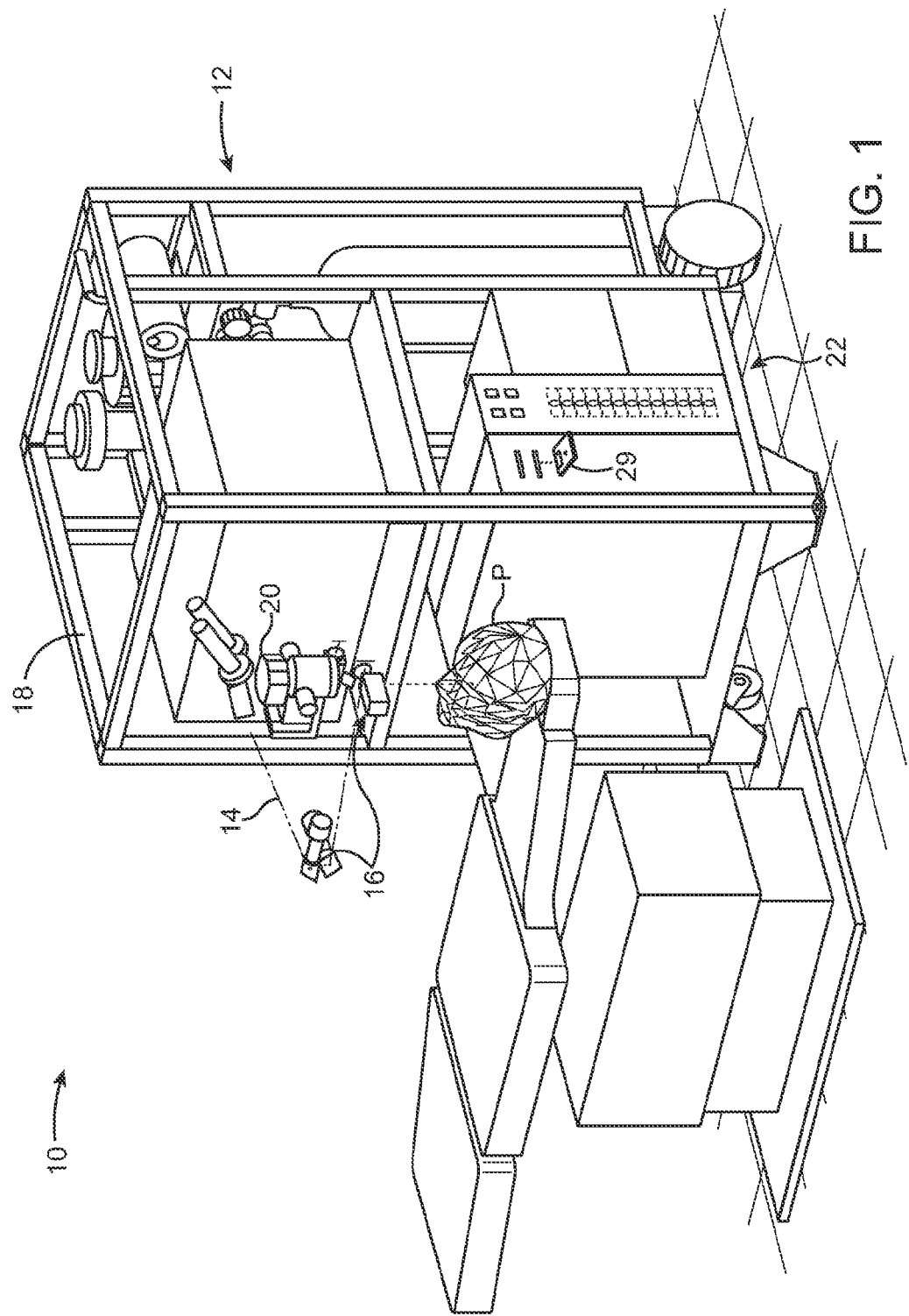
FIG. 1 illustrates a laser ablation system which can be used with a wavefront measurement system.

The present invention may be particularly useful for enhancing the accuracy and efficacy of laser eye surgical procedures, such as photorefractive keratectomy (PRK), phototherapeutic keratectomy (PTK), laser in situ keratomileusis (LASIK), and the like. Enhanced optical accuracy of refractive procedures may be provided by improving the methodology for deriving a corneal ablation or other refractive treatment program. Enhanced accuracy of laser system calibration prior to patient treatment may also be available by providing improved measurements of lenses ablated during system calibration. The techniques described herein can be readily adapted for use with existing laser systems, wavefront sensors, and other optical measurement devices. By providing a more direct (and hence, less prone to noise and other error) methodology for measuring and correcting errors of an optical system, these techniques may facilitate sculpting of the cornea so that treated eyes regularly exceed the normal 20/20 threshold of desired vision. While these systems, software, and methods are described primarily in the context of a laser eye surgery system, alternative eye treatment procedures and systems such as spectacle lenses, intraocular lenses, contact lenses, corneal ring implants, collagenous corneal tissue thermal remodeling, and the like may also be employed.

Wavefront sensors will typically measure aberrations and other optical characteristics of an entire optical system. The data from such a wavefront sensor may be used to generate an optical surface from an array of optical gradients. The optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients or other information should correct the optical tissue system. As used herein the terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure).

In general, techniques for mathematical modeling an optical surface can employ the use of gradient fields comprising several localized gradients of an optical wavefront measured over an area of the optical surface. A localized gradient is often calculated by determining a location of a beam of light corresponding to a small portion of the optical surface. Several localized gradient measurements are made over the measurement area, and the location of each of several beams of light are be determined to map out a gradient field. Some systems, such as Shack-Hartmann wavefront systems form several beams of light simultaneously. Other optical systems measure gradient fields by sequentially measuring gradients at several locations over the measurement area. Determining the exact location of a beam of light can be difficult, particularly to sub-pixel resolution, and threshold and centroid measurements and calculations are often employed. In optical systems which simultaneously form several beams of light, such as with Shack-Hartmann wavefront systems, search algorithms are often employed to determine the location of each of several beams of light on a sensor array.

Wavefront measurement systems can make use of adaptive optics systems such as those including a deformable mirror or the like. Adaptive optics systems are well-suited for measuring a patient's ocular aberrations, often by driving the deformable mirror to a configuration which compensates for the overall aberration of the eye. Using an adaptive optics system, the patient may view optometric test targets (such as an eye) chart to test the subjective visual acuity and contrast sensitivity. Systems and methods for the treatment of presbyopia with adaptive optics are more fully described in U.S. patent application Ser. No. 11/156,257 filed Jun. 17, 2005 (now U.S. Pat. No. 7,513,620), and entitled "Correction of Presbyopia Using Adaptive Optics and Associated Methods," the full disclosure of which is incorporated herein by reference.

Referring now to FIG. 1, a laser eye surgery system 10 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. Alternative sources of ultraviolet or infrared radiation may also be used, particularly those adapted to controllably ablate the corneal tissue without causing significant damage to adjacent and/or underlying tissues of the eye. In some embodiments, the laser beam source employs a solid state laser source having a wavelength between 193 and 215 nm as described in U.S. Pat. Nos. 5,520,679 and 5,144,630 to Lin and 5,742,626 to Mead, the full disclosures of which are incorporated herein by reference. In some embodiments, the laser source includes an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss Meditec, and the like.

Figure 2:
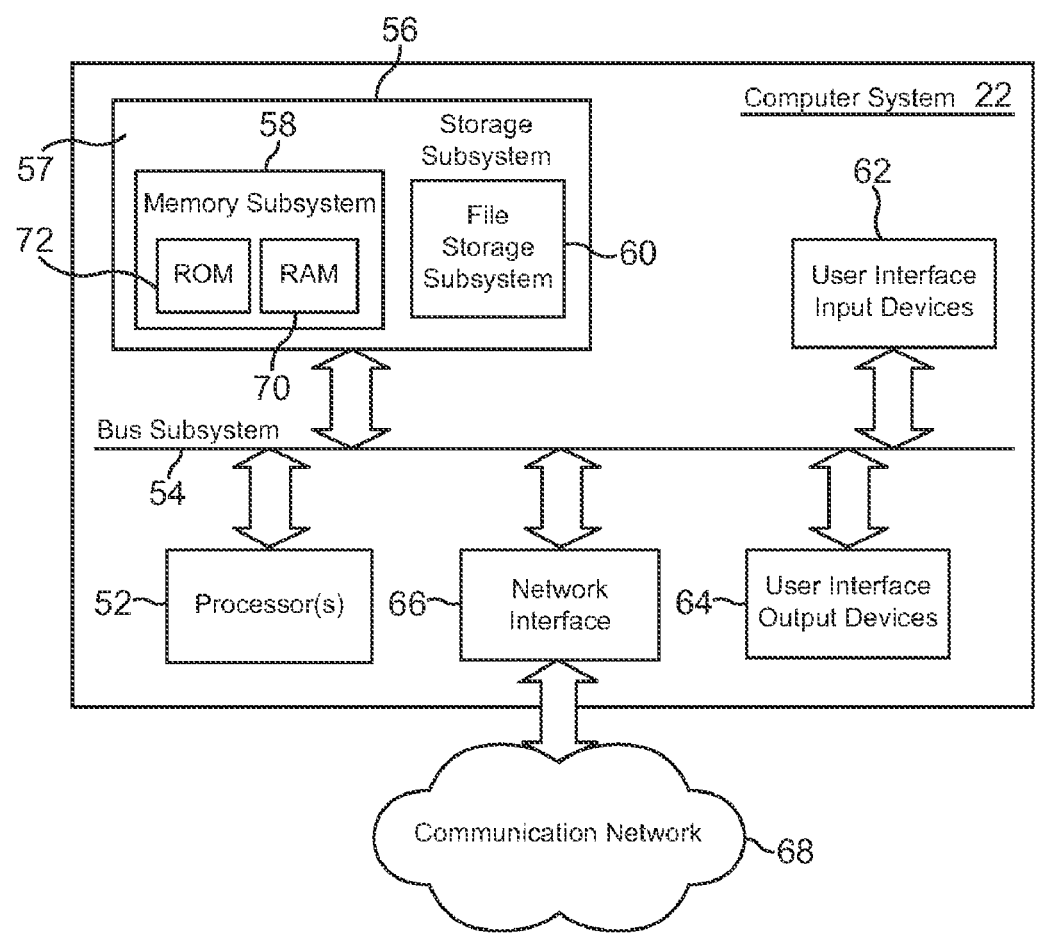
FIG. 2 illustrates a simplified computer system which can be used with the laser ablation system and/or the wavefront system.

FIG. 2 is a simplified block diagram of an exemplary computer system 22 that may be used by laser surgical system 10. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into a display 28, audio input devices such as voice recognition systems, microphones, and other types of input devices. User input devices 62 will often be used to download a computer executable code from a tangible storage media 29 embodying any of the methods described herein.

User interface output devices 64 may include display 28, a printer, a fax machine, or non-visual displays such as audio output devices. The display may be a cathode ray tube (CRT), a flat-panel device such as a liquid crystal display (LCD), a projection device, or the like. The display may also provide a non-visual display such as via audio output devices.

Storage subsystem 56 stores the basic programming and data constructs that provide the functionality of the various embodiments of the methods described herein. For example, a database and modules implementing the functionality of the methods, as described herein, may be stored in storage subsystem 56. These software modules generally are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of program instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM. One or more of the drives may be located at remote locations on other connected computers at other sites coupled to computer system 22. The modules implementing the functionality of the techniques described herein may be stored by file storage subsystem 60. Storage sub system 56 can include any computer readable storage medium 57. For example, computer readable storage medium 57 can include any computer readable storage medium described in the memory subsystem and any computer readable storage medium described in the file storage system. For example, computer readable storage medium 57 can include temporary storage in the random access memory.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example illustrating one embodiment. Many other configurations of computer system 22 are possible having more or less components than the computer system depicted in FIG. 2.

Figure 3:
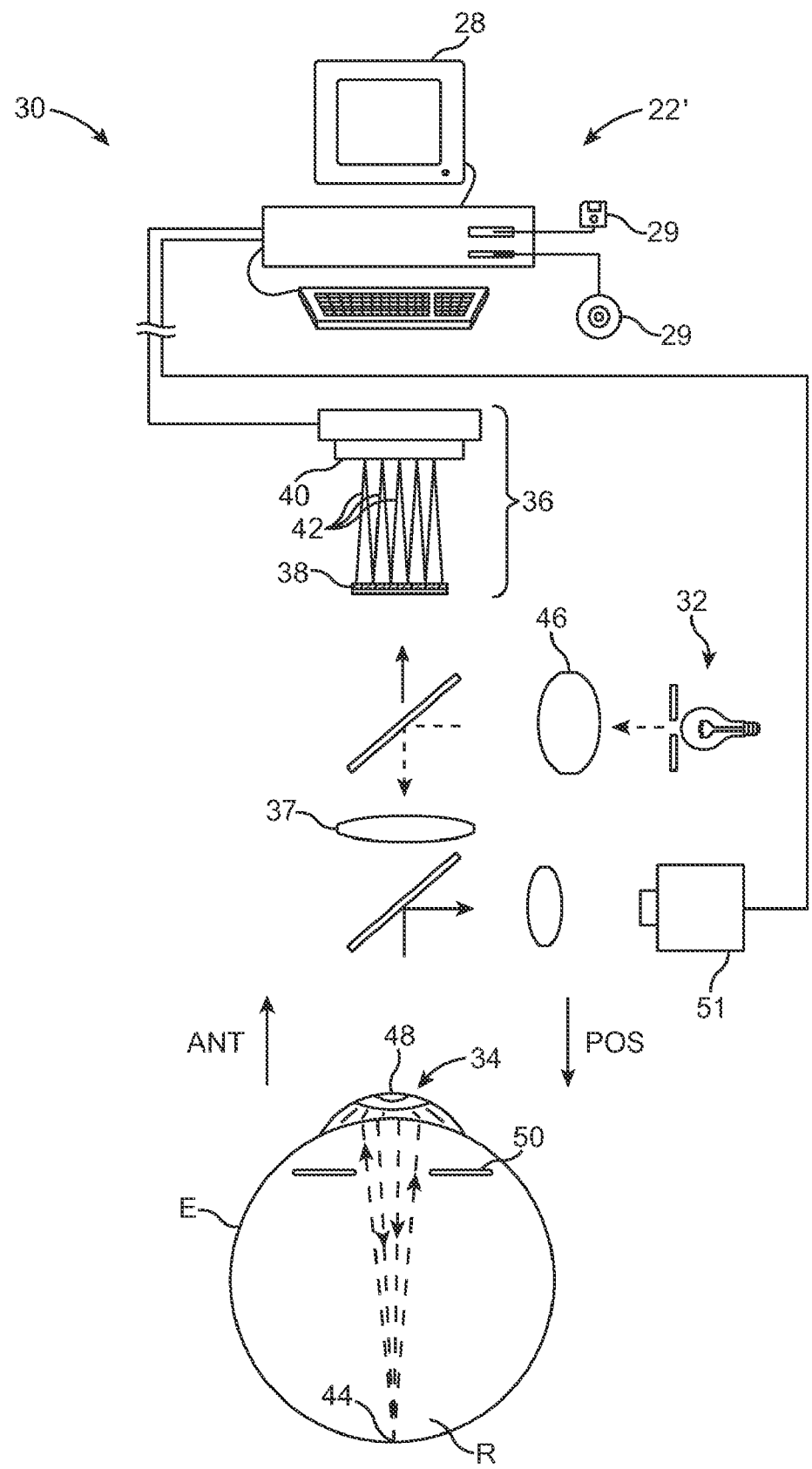
FIG. 3 illustrates a wavefront measurement system capable of measuring eyes.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Wavefront system 30 generally can include a lenslet array to sample the gradient map uniformly over an aperture, which is typically the exit pupil of the eye. Thereafter, the local slopes of the gradient map can be analyzed so as to reconstruct the wavefront surface or map.

More specifically, wavefront measurement system 30 can include an image source 32, such as a laser, which projects a source image through optical tissues 34 of eye E so as to form an image 44 upon a surface of retina R. Image 44 can comprise a very tiny spot of light and can be formed by imaging light passing through an aperture positioned near source 32. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include tangible media embodying instructions or code for characterizing a surface, and/or for the other methods described herein. For example, instructions measuring a wavefront elevation profile by mapping data to signals in transform space and mapping the signals in transform space to the wavefront elevation profile. Computer 22' may include the same or similar hardware as the computer system 22 illustrated in FIGS. 1 and 2. Computer system 22' may be in communication with computer system 22 that directs the laser surgery system 10. If desired, data from wavefront sensor 36 may be transmitted to a laser computer system 22 via tangible media 29, via an I/O port, via an networking connection 66 such as an intranet or the Internet, a local area network (LAN) or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue. In alternate embodiments, the sensor can comprise a linear array detector, orthogonal linear array detectors, a position sensing detector or a quadrant detector.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. As image 44 is actually formed on retina R, image 44 may be distorted by any imperfections in the eye's optical system. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

The wavefront data may be stored in a computer readable medium 29 or a memory of the wavefront sensor system 30 in three separate arrays containing 1) the light spot pattern, 2) the x and y wavefront gradient values obtained from image spot analysis of the Hartmann-Shack sensor images, and 3) the x and y pupil center offsets from the nominal center of the Hartmann-Shack lenslet array, as measured by the pupil camera 51 (FIG. 3) image. Such information can contain all the information on the wavefront error from one or more wavefront measurements of the eye and is sufficient to reconstruct the wavefront or any portion of it. In other embodiments, the wavefront data may be stored in a memory of the wavefront sensor system in a single array or multiple arrays. In many embodiments additional patient data can be stored such as manifest patient refraction, subjective patient needs and preferences, and data measured with other instruments. While the computer readable medium or memory is shown with respect to the wavefront sensor system, additional memory and computers can be used. For example, computers sharing information over the local area network (LAN), and the intranet, and the Internet.

While methods will generally be described herein with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 4:
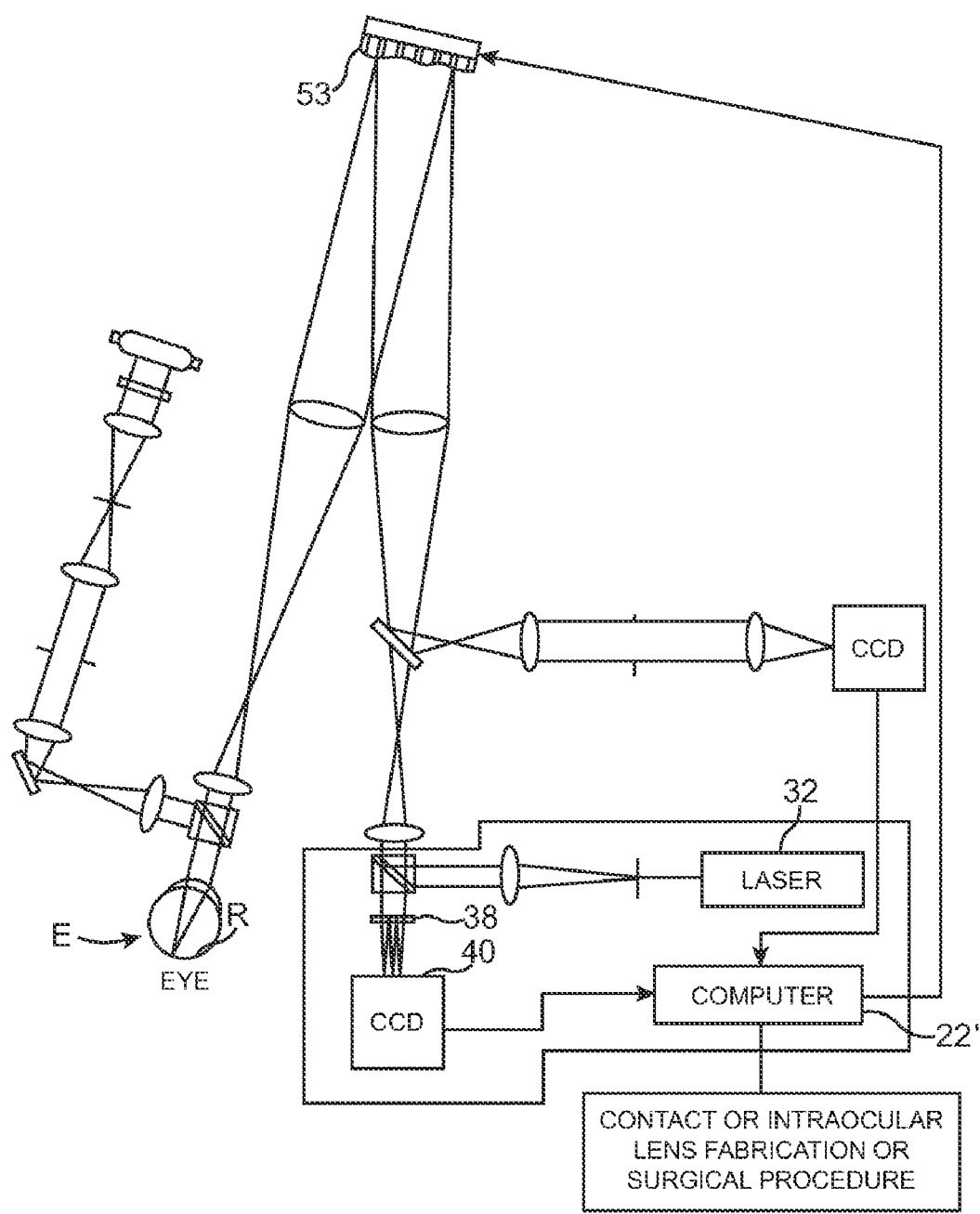
FIG. 4 illustrates another wavefront measurement system capable of measuring eyes and incorporating an adaptive optic.

An alternative embodiment of a wavefront measurement system is illustrated in FIG. 4. The major components of the system of FIG. 4 are similar to those of FIG. 3. Additionally, FIG. 4 includes an adaptive optics system 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 4 are more fully described in U.S. Pat. No. 6,095,651, the full disclosure of which is incorporated herein by reference.

The components of an embodiment of a wavefront measurement system for measuring the eye and ablations comprise elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Figure 5:
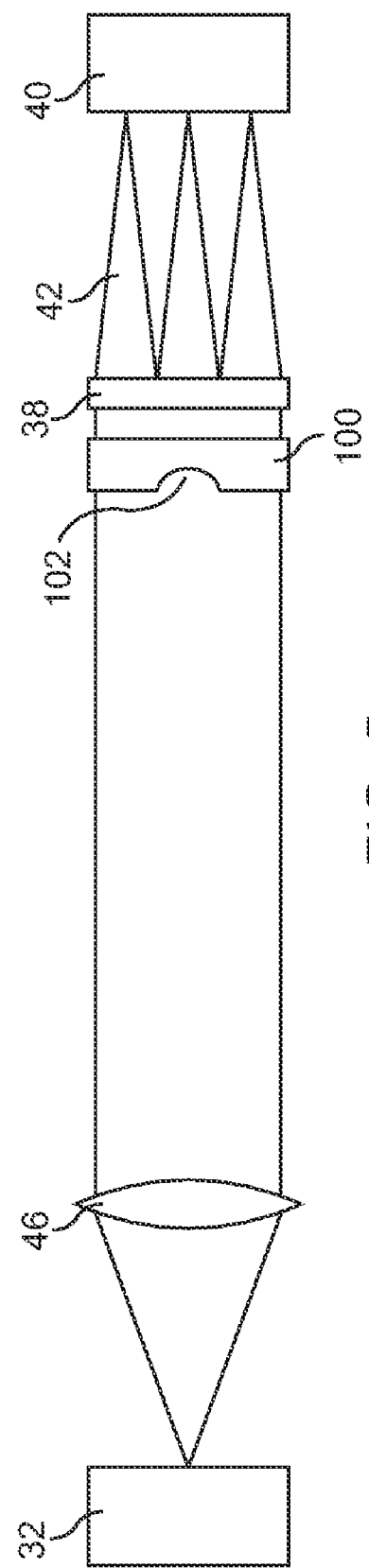
FIG. 5 illustrates a wavefront system capable of measuring ablated surfaces.

An alternative embodiment of a wavefront measurement system suitable for measuring ablated surfaces is illustrated in FIG. 5. The major components of the system of FIG. 5 are similar to those of FIGS. 3 and 4 shown above. A source 32 projects light along an optical path. An optic 46 collimates light from the source. An optical surface 102 is formed in a material 100. Optical surface 102 can be an ablation and material 100 can be transparent. Light energy passes through material 100 which is positioned near lenslet array 38. The lenslet array separates the transmitted image into an array of beamlets 42, and images and/or focuses the separated beamlets onto the surface of sensor 40 as described above. Sensor 40 typically comprises a charged couple device or "CCD," and senses the characteristics of these individual beamlets as described above. In particular, where image 44 comprises a point or small spot of light, a location of the transmitted spot as focused by a lenslet can directly indicate a local gradient of the associated region of the optical surface 102. In an alternate embodiment, light rays can be projected onto an optical surface, such as a corneal of an eye or an ablation formed in plastic, and reflections of light from the surface are measured with a wavefront sensor. For example, U.S. Pat. No. 5,062,702, the full disclosure of which is incorporated herein by reference, illustrates a wavefront sensor for measuring a corneal surfaces which can incorporate the techniques described herein.

In exemplary embodiments, the laser system can be calibrated using measurements of optical surfaces ablated in plastic. At least one object, preferably a transparent calibration plastic, is ablated with the laser system to form an optical surface in the plastic. For example, test ablations having optical powers in Diopters of −6 D, +4 D and 0 D can be made in plastic. The optical surfaces ablated in the plastic object are determined, calculated and/or measured with any of the wavefront systems and methods described herein. The measured power of the ablated optical surface is compared to an intended power of the ablated optical surface. If the measured optical power of the ablated optical surface is within a predetermined tolerance range, no further adjustment is needed. However, if the measured optical surface is outside the predetermined tolerance range, the laser system can be adjusted. The laser system can be adjusted in response to the measured optical surface and optical power of the surface such as the lenses described above. An output energy level of the laser can be adjusted from a first output energy to a second output energy. Alternatively, calculations made with the processor can be adjusted. For example basis functions and scaling factors as described in U.S. Pat. No. 7,008,415, the full disclosure of which is incorporated herein by reference can be adjusted. After the laser system is adjusted, additional test ablations are made in plastic test object(s) and the measured optical surface is compared to the intended optical surface. The above steps can be repeated until the laser system ablates optical surfaces within the predetermined tolerance ranges.

The techniques described herein can be incorporated into many known surface topography and wavefront systems such as Shack-Hartmann, Tschening aberrometry, and Moire deflectometry wavefront systems, and topography systems generating data with light intensity patterns. For example, U.S. Pat. No. 5,339,121, the full disclosure of which is incorporated herein by reference, describes a corneal topography machine in which a rectilinear grid is projected onto a cornea. Images of light intensity patterns from this device can be acquired as physical location data and mapped to signals in transform space. The signals from transform space can be analyzed and/or mapped back to physical space to determine optical surface characteristics of the cornea, for example an elevation map of the surface of the cornea. U.S. Pat. No. 6,932,475, the full disclosure of which is incorporated herein by reference, describes a device for measuring aberrations of the eye. This device can sequentially scan locations of the eye with a light beam and image the light beam onto a photodetector, often linear and orthogonal X and Y detectors, which can measure the position of probing beam light scattered back from the retina of the eye, so as to measure aberration and refraction of the eye at a plurality of locations. Light patterns acquired with this device can be mapped to transform space, and signals from transform space can be analyzed and/or mapped back to physical space to determine aberrations of the eye.

Figure 6:
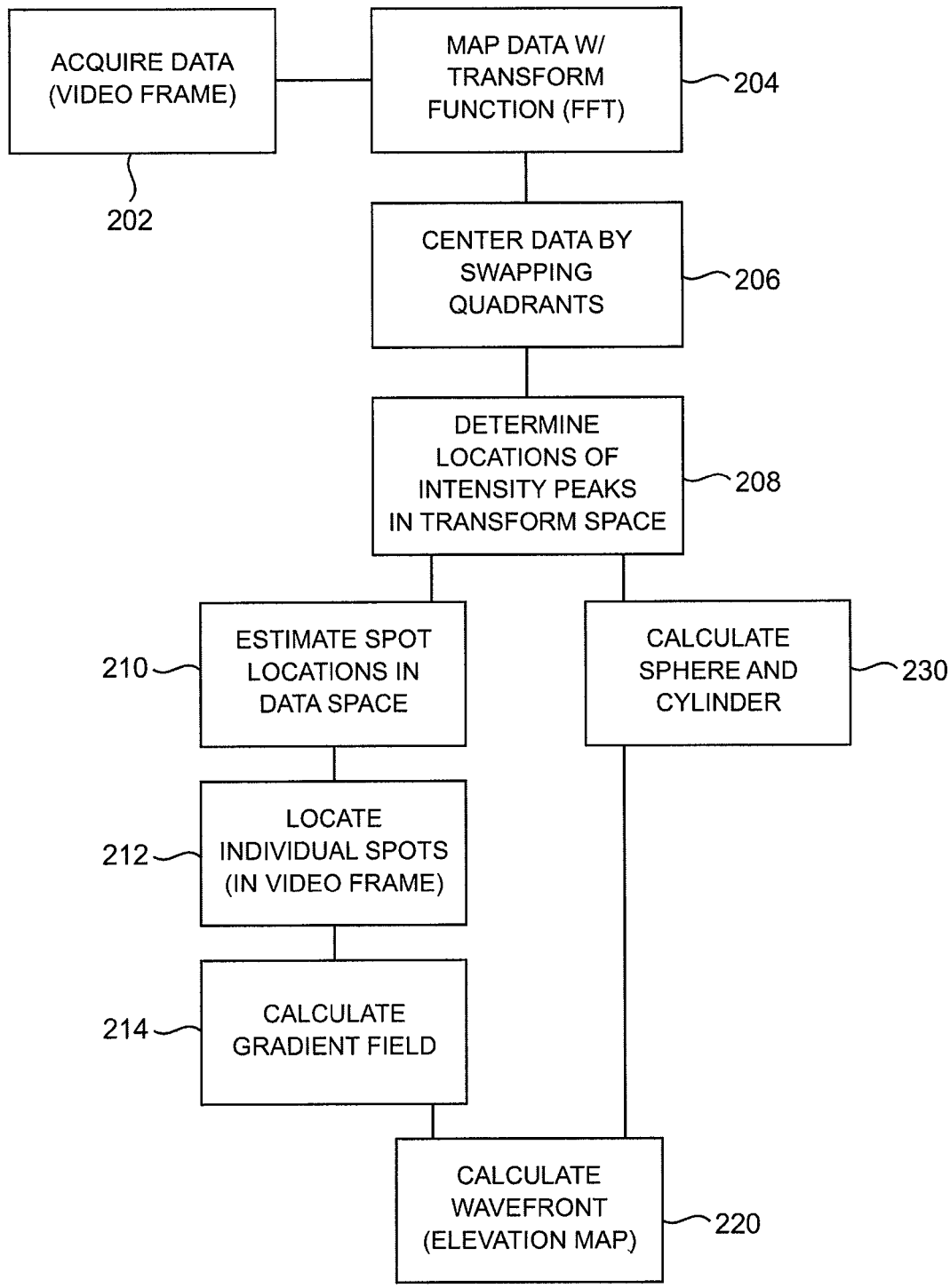
FIG. 6 is a flow chart schematically illustrating a method for determining a wavefront, and/or modules or blocks of a computer program for implementing the method.

Referring now to FIG. 6, techniques 200 are illustrated, which can be combined with any of the wavefront systems described above to measure an optical surface. These techniques can be implemented with the processor shown above, and can be implemented as machine readable code embedded in a tangible media as described above. In embodiments, the techniques illustrated in FIG. 6 correspond to a flow chart of an algorithm for determining characteristics of a wavefront, and/or blocks of a computer program implementing the techniques. Data is first acquired at step 202. Data acquisition can be from a CCD array, line sensor or scanner, analog position sensor, quadrant detector or any device which converts light energy into an electronic signal. Data acquired in step 202 can be stored in the memory of the processor. The data is mapped with a transform function to a transform space at step 204. Step 204 can be performed with a Fourier transform which maps the acquired data to frequency space. The data in frequency space is centered by swapping quadrants at step 206. Locations of intensity peaks are determined at step 208. The locations of the intensity peaks can be spatial frequency intensity peaks in a two dimensional frequency space, in which the peaks are located at characteristic frequencies in the two dimensional frequency space.

In many embodiments, the location of light spots in the acquired data can be estimated at step 210. This estimation can be made using the frequencies determined at step 208. Using the estimated location of the light spots, individual light spots can be located at step 212. A gradient field for the wavefront can be calculated at step 214. From this gradient field the wavefront of the optical surface can be calculated at step 220.

Exemplary embodiments can calculate sphere and cylinder of the optical surface directly from the transform space as illustrated at step 230. These embodiments can benefit from determining the characteristics of optical surface without having to determine the location of individual spots. The sphere can cylinder determined at step 230 can be used to calculate a wavefront elevation map of the optical surface at step 220.

Figure 6A:
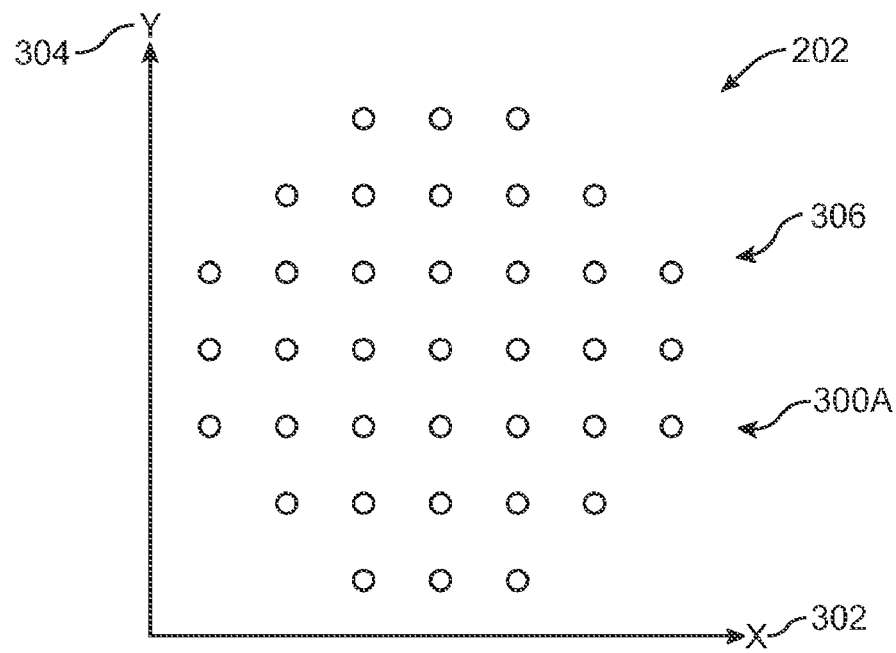
FIGS. 6A and 7A illustrate light energy patterns and acquired data.
Figure 6B:
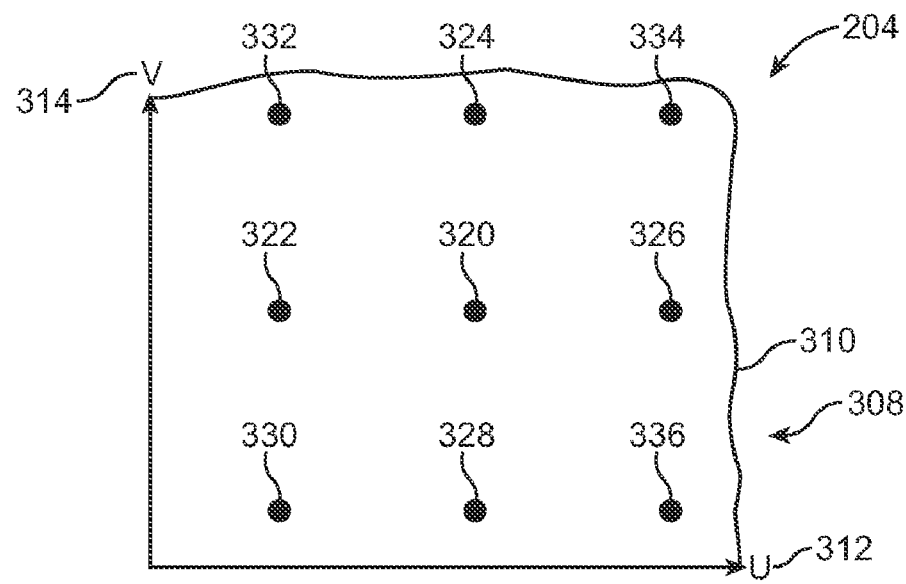
FIGS. 6B and 7B illustrate a mapping of light energy pattern data from physical coordinate locations as illustrated in FIGS. 6A and 7A to coordinate locations in a transform space
Figure 6C:
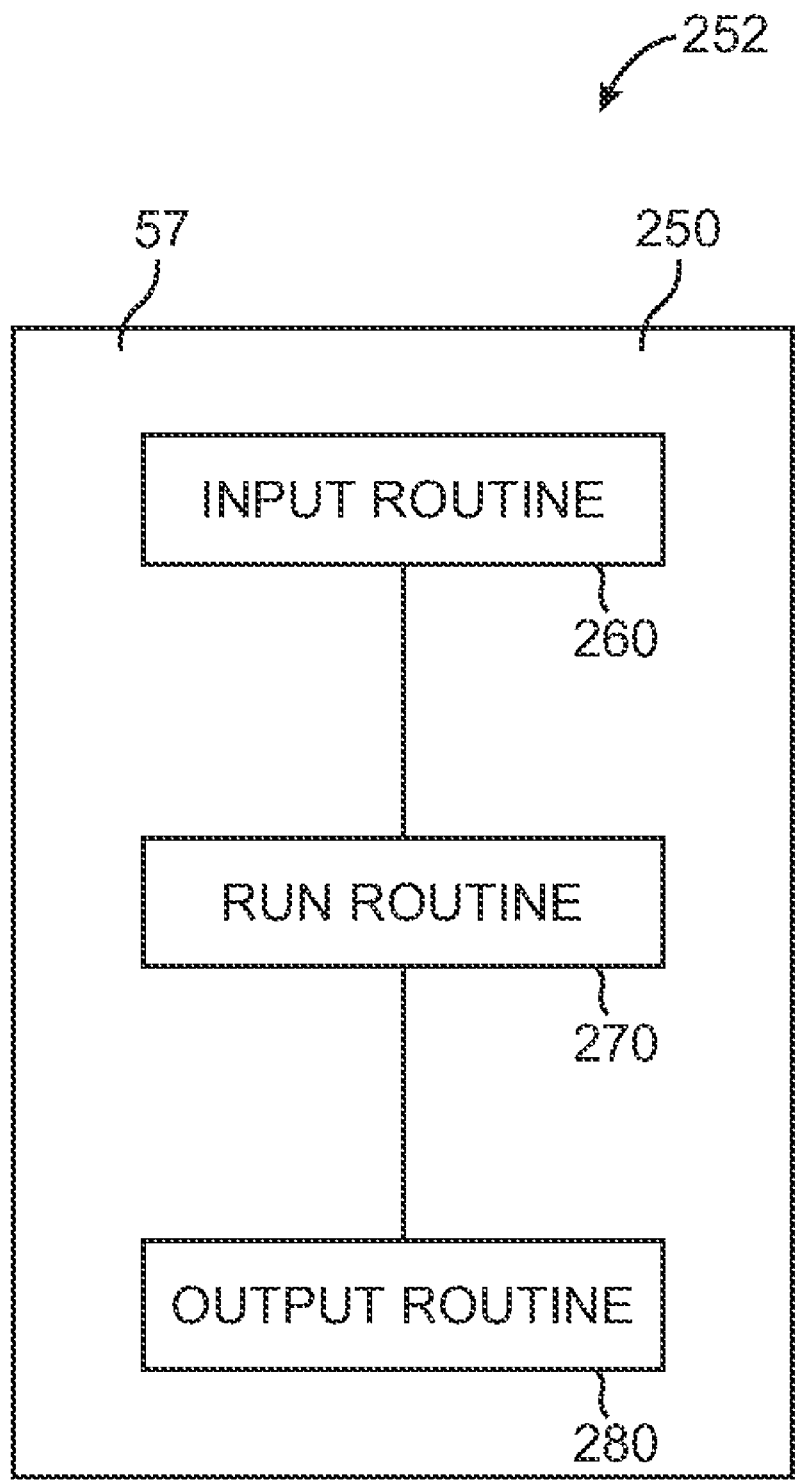
FIG. 6C illustrates a simplified flow chart of a computer-readable storage medium having a set of instructions that can be read by a computer to determine an optical characteristic of an object.

FIG. 6C illustrates a computer-readable storage medium 57 having a set of instructions 252 for a computer to determine an optical characteristic of an object, for example the optical surface of the eye as shown above. Medium 57 can include a variety of tangible media as described above. In particular, the storage medium can be RAM which temporarily stores the set of instructions. This temporary storage can occur on a client computer or server computer or both, or a computer which is not connected to another computer with a network or the like. The set of instructions can be loaded onto the medium by any means including transferring set of instructions 252 from the Internet, the intranet, the LAN, the floppy drive, the CD ROM drive and the flash RAM such as a jump drive. The set of instructions can include an input routine 260, a run routine 270, and an output routine 280. Input routine 260 can be operatively associated with a source of detector data. For example input routine 260 can cause the acquisition of light pattern data from a CCD array as described with regard to step 202 herein, and read this data into the computer RAM. Alternatively, input routine 260 could read data from the internet, an intranet, a LAN or the like, so as to make the data available for analysis. Run routine 270 uses a transform function (which can be any function) to map the data to an array which corresponds to signals in the transform space, which can be any transform space. Run routine 270 can determine the optical characteristic of the object from the signals in transform space, for example the optical surface of the object. Run routine 270 can implement any combination of steps 204, 206, 208, 210, 212, 214, 220 and 230 as described herein. After the optical characteristic of the object has been determined, an output routine makes the optical characteristic available for external use outside the computer. For example a wavefront data map can be displayed on the visual display. The coefficients of sphere and cylinder can be displayed on the visual display. The optical characteristic can be displayed as a target correction to a patient. Information derived from the optical characteristic can be made available for external use outside the computer, for example a target amount of tissue to be removed and a laser treatment table calculated from the optical characteristic as described herein.

2. Mapping Data From Physical Data Space to Transform (Frequency) Space

Figure 7A:
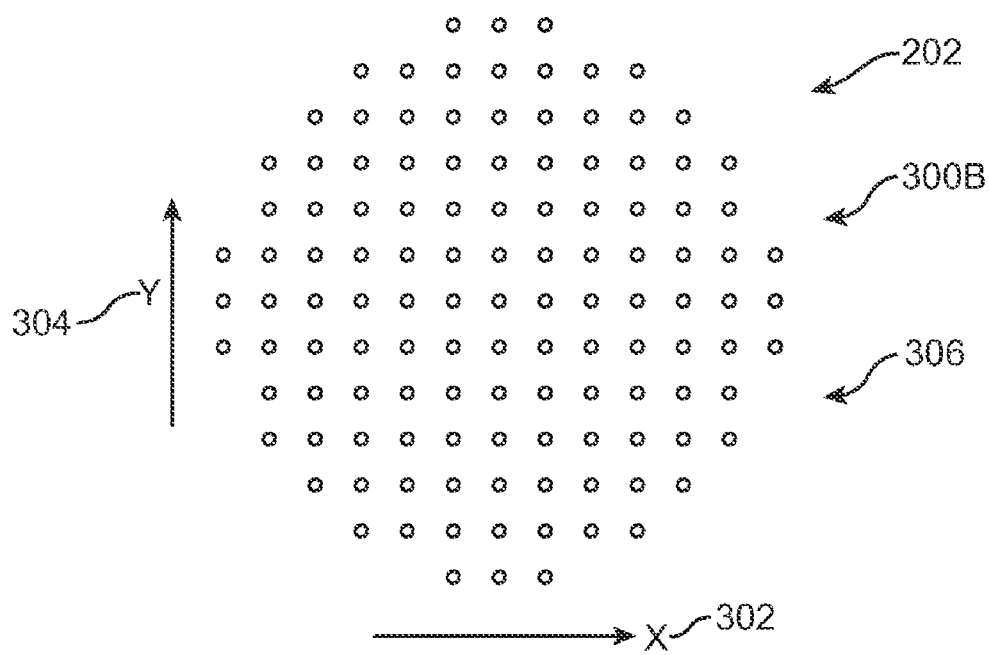

Referring now to FIGS. 6A and 7A, data acquired at data acquisition step 202 are illustrated. Several spots of light 300A and 300B are acquired as a video frame of data. Several video frames of data can be averaged to provide an improved signal to noise ratio. Spots of light on an array can have an irregular spacing as with 300A, or a regular spacing as with 300B. The acquired data can correspond to a physical location on the detector. The physical location of spots of light can correspond to coordinate references X 302 and Y 304. For convenience, the physical location of the spots of light on a detector along the coordinate references X 304 and Y 306 can be referred to as locations in data space 306.

Figure 7B:
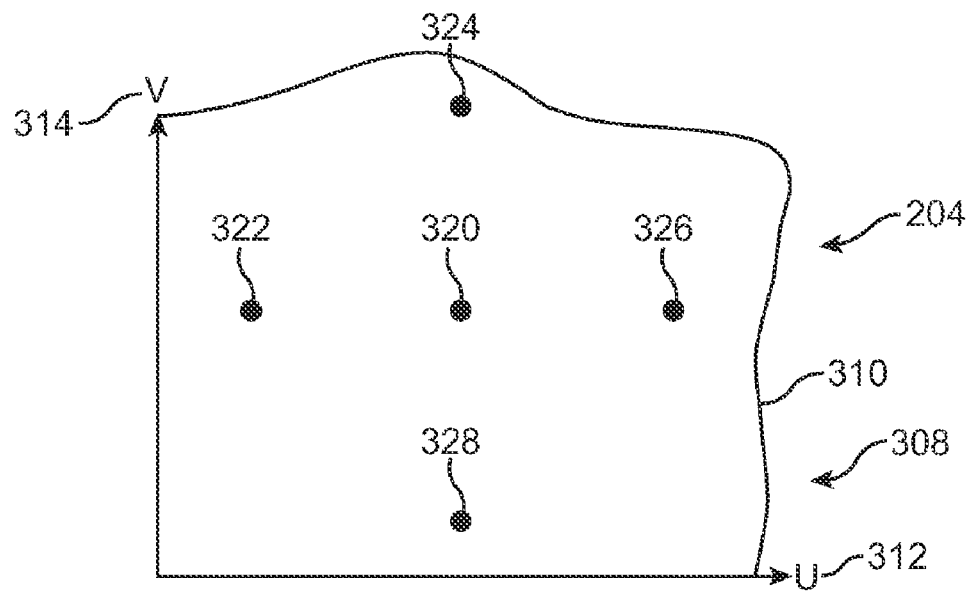

Referring now to FIGS. 6B and 7B, a mapping of the data from data space to a transform space as in step 204 is illustrated. A first coordinate reference in a transform space 308 is a horizontal spatial frequency dimension 312. A second coordinate reference in transform space 308 is a vertical spatial frequency dimension 314. Mapping of the data from data space 306 to transform space 308 may accomplished with any transform function such as a Fourier transform, discrete Fourier transform, Hadamard transform, chirp functions and a Laplace transform. Other suitable transform functions can be developed as appropriate. Mapping data from physical space to transform space can produce an array of numbers in which each value of the array is a signal in transform space. For example, mapping a two dimensional data array of a light pattern to transform space can produce a two dimensional data array in which each value of the array corresponds to a signal in transform space. For example, mapping the acquired data to a plane 310 in transform space 308 can produce signals in transform space. These signals in transform space corresponding to localized spatial frequency intensity peaks 320, 322, 324, 326, 328. Additional peaks 330, 332, 334 and 336 may be present, in addition to other peaks not shown, depending on the characteristics of the acquired data. The data mapped with the transform function can be stored in an array of the processor. While step 204 can be performed with the processor, other techniques can be employed to transform the light pattern, such as an optical Fourier transform which maps intensity to frequency space. If desired, steps of the techniques can be performed in any order. For example, with an optical Fourier transform the data acquisition step 202 can be performed after the mapping step 204.

Figure 8:
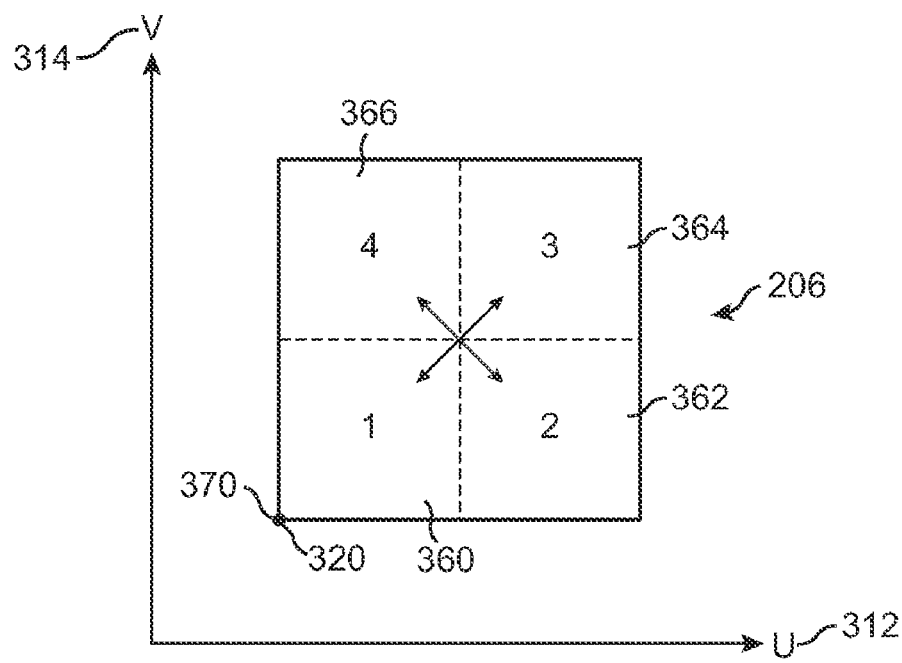
FIGS. 8 and 8A illustrate swapping quadrants of transformed data to position an origin of the transform space coordinate system near a central location of the transform array.
Figure 8A:
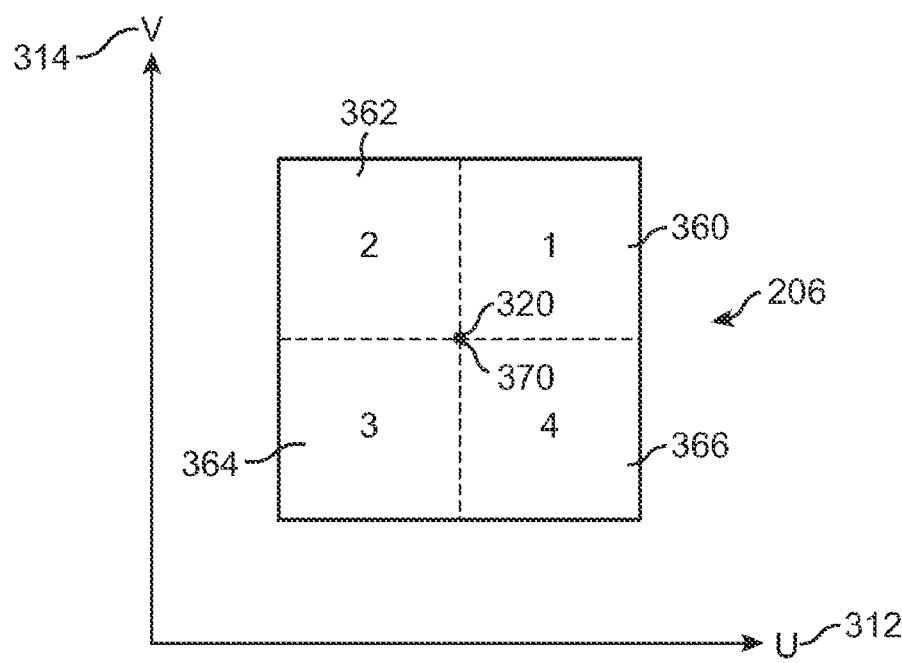

In embodiments illustrated by FIGS. 8 and 8A at step 206, quadrants of the array map in frequency space can be manipulated to make data easier to interpret. In particular, data of the array can comprise a first quadrant 360, a second quadrant 362, a third quadrant 364, and a fourth quadrant 366. An origin 370 of a coordinate system in transform space 308 may not be located at the center of an array as illustrated in FIG. 8. By swapping the first quadrant with the third quadrant and the second quadrant with the fourth quadrant, the origin of the coordinate system appears centered in the data array. This technique can be particularly helpful with maps using Fourier transforms because the origin 360 of such a system corresponds to frequencies of 0 Hertz.

Figure 9:
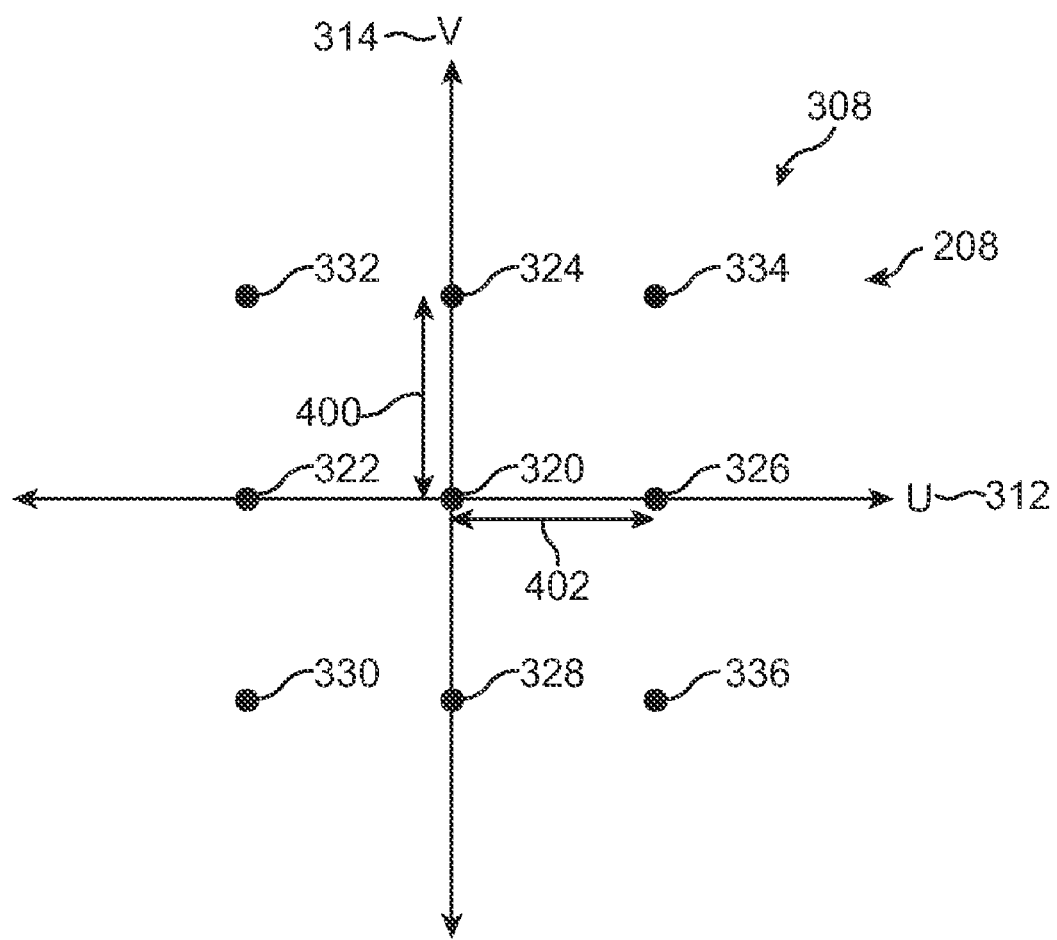
FIG. 9 illustrates characteristic locations and intensities of signals in a transform space.

Referring now to FIG. 9, locations of intensity peaks in transform space can be located in accordance with step 208. A central peak 320 can be located at the origin. Other peaks 322, 324, 326, 328, 330, 332, 334 and 336 can be located in the transform space near the central peak. Peak 324 is located near the origin along the vertical spatial frequency dimension 314. Peak 324 has a coordinate reference 400 which locates the peak along vertical frequency dimension 314. Coordinate reference 400 corresponds to a characteristic frequency along vertical frequency dimension 314. The frequency of this peak along the vertical frequency dimension can be determined by measuring a centroid of the peak from the array. Peak 326 is located near the origin along the horizontal spatial frequency dimension 312. Peak 326 has a coordinate reference 402 along horizontal frequency dimension 312 which locates the peak along horizontal frequency dimension 312. Coordinate reference 402 corresponds to a frequency along horizontal frequency dimension 312. The characteristic frequency of this peak along the horizontal frequency dimension can be determined by measuring a centroid of the peak from the array. Locations of additional peaks along horizontal and vertical frequency dimensions can also be measured. For example, peak 334 has a horizontal spatial frequency coordinate reference of 402 which locates peak 334 along the horizontal spatial frequency dimension, and a vertical spatial frequency coordinate reference 400 which locates the peak along the vertical spatial frequency dimension. Peak 334 has two characteristic frequencies which determine the location of the peak in the spatial frequency plane.

3. Estimation of Spot Location in Physical Data Space

Figure 10:
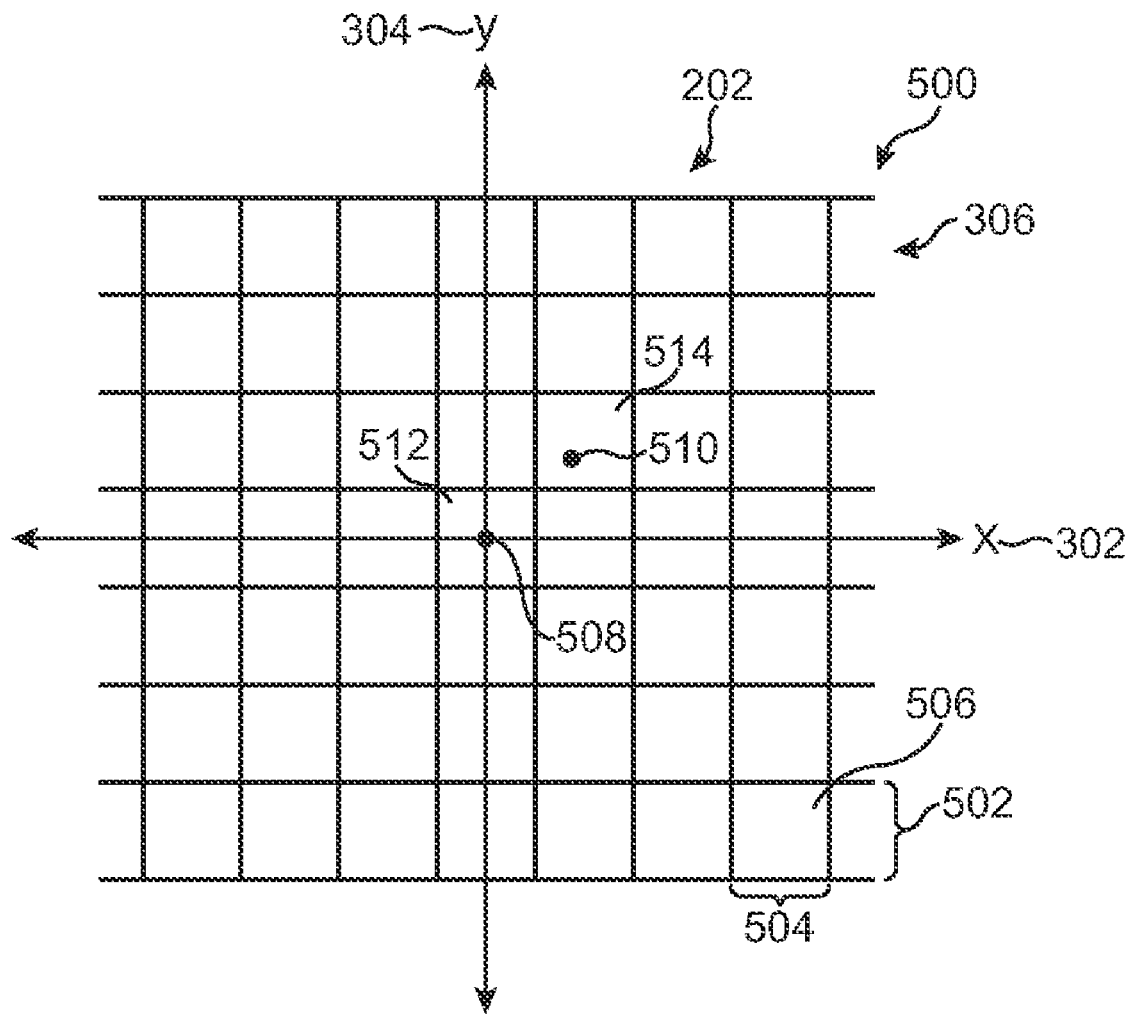
FIG. 10 illustrates estimates of locations of spots of light energy in a light energy pattern.

Referring now to FIG. 10, spot locations are estimated and located in accordance with embodiments. In embodiments of the invention illustrated at steps 210, 212 and 214 of FIG. 6, the frequencies corresponding to spatial frequency intensity peaks are used to estimate and locate positions of spots of light in a video frame. These locations can be used to calculate the gradient field. An acquired data frame 202 is divided into sections with a grid 500. Grid 500 can be comprised of several discrete rectangular sections such as section 506 having a vertical separation distance 502 between horizontal rows of the grid and a horizontal separation distance 504 between vertical rows of the grid. The position of the light spots can be estimated to be at a central location of each rectangular section such as section 506. Positions individual light spots such as central light spot 508 and an adjacent light spot 510 are located within each section of the grid. For example, light spot 508 is located in section 512, and light spot 510 is located in section 514. An algorithm which locates spots can be programmed so as to search for each spot within each section of the grid. The sections of the grid can be determined prior to locating the positions of the spots of light. Alternatively the sections of the grid which are searched to find the location of the spot of light can be determined dynamically as the spots are located. For example, after a first spot such as spot 508 is located, a search area adjacent to spot 508 can be defined using the horizontal and vertical distances and the location of spot 508 so as to define a second search area. A local gradient of the optical surface can be calculated for each light spot located. The gradient field is calculated by determining local gradients for several light spots in the grid. The wavefront of the optical surface can then calculated from the gradient field by any number of methods, including those described above.

In embodiments using CCD sensors, it may be convenient to estimate locations of the spots of light in terms of pixels. In these embodiments the spacing of the pixels about a central light spot as shown above can be given by the formula delta_x=M/delta_fx delta_y=N/delta_fy where delta_fx is the frequency location of the spatial frequency intensity peak disposed along the horizontal frequency dimension as shown above, M is the number of horizontal pixels (often 640) and delta_x is the estimated horizontal spacing between the pixels of the light spots. Similarly, delta_fy is the frequency location of the spatial frequency intensity peak disposed along the vertical frequency dimension, N is the number of vertical pixels (often 480) and delta_y is the estimated vertical spacing between the pixels.

Examples of estimated spacing of light spots in units of pixels in horizontal and vertical dimensions are shown below in Table 1 for each of 3 ablations having refractive powers of −6, +4 and 0 Diopters. The estimated values are compared to values measured by locating individual spots as described above. For the −6 D ablation the estimated spacing between light spots along the horizontal and vertical dimension are 40 and 43.6 pixels respectively, and the average value determined by locating the spots is 41.2 pixels. For the 0 D ablation (an ablation in plastic having a uniform depth of approximately 50 microns) the estimated spacing between light spots along the horizontal and vertical dimension are 30.5 and 30 pixels respectively, and the average value determined by locating the spots is 30 pixels. For the +4D ablation the estimated spacing between light spots along the horizontal and vertical dimension are 23.7 and 24 pixels respectively, and the average value determined by locating the spots is 25 pixels.

TABLE 1

Comparison of estimated spacing between spot locations with averages of values between located spots (units in pixels).

| Ablation | Estimate X | Estimate Y | Average of Measured Values |
| --- | --- | --- | --- |
| −6 D | 40 | 43.6 | 41.2 |
| 0 D | 30.5 | 30 | 30 |
| +4 D | 23.7 | 24 | 25 |

4. Rapid Determination of Wavefront Error Using Transform Methods and Calculations In exemplary embodiments illustrated as steps 230 and 220 of FIG. 6, the optical surface can be characterized using the information from the transform map, often without determining the location of individual spots of light. These steps can be understood first with reference to 1) mapping of discrete location data space to discrete frequency space via a discrete fast Fourier transform; 2) the action of a sphero cylindrical non-zero wavefront on a Shack-Hartmann pattern; and 3) a review of the method.

4.1 Mapping of Discrete Data from Physical Data Space to Spatial Frequency Space Via a Discrete Fast Fourier Transform Real data is generally collected at discrete locations corresponding to locations in a data space, and a real data set is generally limited in size. In some embodiments, the data can be collected on a regular grid so that collection points are evenly spaced apart. This can be an excellent representation of intensity data collected by a CCD array as the data can consist of the intensity values found on each element (or pixel) of the sensor that are in turn generally located at the same distance from their neighbors. When a discrete Fourier transform is taken on such a data set to map data from physical data space to a frequency space, it can be done (in the case of one dimension) using the formula $$F(k) = \sum_{n=1}^{N} f(n) e^{-i2\pi \frac{(k-1)(n-1)}{N}} \qquad (1)$$

where n is an index specifying the location on the grid f(n) is the data value at location n N is the total number of data locations in the data set k is a spatial frequency F(k) is the value—usually complex—at spatial frequency k In similar fashion, if the spatial frequency array F is given (in one dimension corresponding to signal values in frequency space), the data array corresponding to light intensity values in physical data space can be found using the formula for inverse discrete Fourier transform.

$$f(n) = \frac{1}{N}\sum_{k=1}^{N} F(k)e^{i2\pi \frac{(k-1)(n-1)}{N}} \quad (2)$$

When the fast Fourier transform is performed, spatial frequency array F is created from data array f and has the same size. Two dimensional data arrays and the techniques for mapping these arrays from data space to frequency space are generally well known in the art. In general two dimensional data arrays can be expressed as an M by N data array in which M is a number of columns of the data array and N is a number of rows of the data array. Thus, if f has a size (M×N) then F can have the size (M×N). From a mathematical point of view then, the fast Fourier transform is a mapping function which transforms data from physical location space to signals in spatial frequency space. Mapping an M×N data array corresponding to M×N data values from physical space to transform space can result in an array corresponding to M×N signals in transform space. Thus, a correspondence can be found between patterns in data in physical location space and the location of characteristic signals and/or peaks in frequency (transform) space. For example, a sinusoidal grating pattern in physical data space can have a characteristic signal frequency corresponding to a spatial frequency intensity peak in frequency space.

An examination of Eq. (2) can show that as a spatial frequency index k is increased from 1 to N, a value in the argument of a complex exponential can increase from a value of 0 when k=1 to $$\frac{i2\pi(N-1)}{N}(n-1) \text{ when } k = N \text{ in steps of } \frac{i2\pi}{N}.$$

However since $$e^{\frac{i2\pi}{N}a} = -e^{\frac{i2\pi}{N}(a+N/2)}$$

it may generally be seen that whenever, for two values of the pairs (n, k) and (n', k') occur such that (n−1)(k−1)=(n'−1)(k'−1)+N/2, the exponentials have equal but opposite values. Thus, if f(n) is a constant, a cancellation can occur. For instance, for a uniform intensity at all points, there can be a cancellation of all terms except the term for k=1, for which the exponential equals 1 and the frequency value is the value of each data point. This result can illustrate, with Fourier transform theory, a constant amplitude function in frequency space transforming to a delta function in physical data space(a function that is generally non-zero at only one location).

For each spatial frequency value in the spatial frequency range from 0 to iπ there may be an identical value occurring in the range iπ to i2π. For two-dimensional Fourier transforms this can mean that the first quadrant is mirrored by the third quadrant and the second quadrant is mirrored by the fourth quadrant.

When the data function only has non-negative values on a regular grid, the spatial frequency array created from it can take the form of a two-dimensional Dirac comb. This pattern can be of especial interest to this investigation as Shack-Hartmann spot patterns can have the characteristic of two-dimensional Dirac combs. Specifically, high light intensity values can be located at regularly spaced intervals over the sampled data array. Since the fast Fourier transform is limited in size, a Dirac comb in one space (e.g. data space) may not create a Dirac comb in the complimentary space (e.g. frequency space) but can create a spectrum that is close to a Dirac comb. A spacing between peaks of a Dirac comb can be referred to as a pitch. To relate the spacing of the peaks in the two Dirac combs, the following formula may be used.

$$pf=N/pd \quad (3)$$

where pd is the pitch of the data grid in physical data space, i.e. the distance in grid increments between successive data peaks pf is the pitch of the spatial frequency grid in frequency space, i.e. the distance in grid increments between successive spatial frequency value peaks N is the number of elements in the grid There will generally exist a value for the spatial frequency 0. This may be seen by examining Eq. (1) for the case k=1, the 0 Hz spatial frequency index value. For this spatial frequency, Eq. (1) gives the average value of the data set and since there are no negative values, the average is nearly always positive and non-zero. However for other spatial frequencies, the peak values can occur at spatial frequencies whose values are spaced at a pitch given by Eq. (3). If in a two-dimensional data array the pitch in the x direction, pdx, is different from the pitch in the y direction, pdy, then the data typically falls on a rectangular grid instead of a square grid and there can be a spatial frequency pitch for a the x dimension, pfx, that is different from the spatial frequency pitch for the y dimension, pfy. Even though the spatial frequency pitches for the two dimensions can be different, Eq. (3) may be used to find both.

As will be found subsequently, it can also be of interest to consider what may happen to the spatial frequency mapping if individual rows and columns take a regular spacing and neighboring rows and columns are shifted with respect to a given row or column by fixed amounts. The resulting pattern is often called a skew-periodic array. These arrays are parallelogram shaped data arrays. This kind of pattern can be addressed with a method describing the types of space distortion that can transform square grids to parallelogram shaped grids.

4.2 Distortion of Skew Periodic Arrays

We can begin by introducing the idea of a transform operator that changes the points in one grid to those in a second grid. The transform can be represented by the action of a matrix, the transform operator, on a vector whose components are the space locations of the points on the grid. The result is generally a second vector whose components are the space location so the points on the transformed grid. In specific embodiments, this operation is just a common mathematical linear transformation. The matrix equation is then $$\begin{pmatrix} x' \\ y' \end{pmatrix} = \begin{bmatrix} a & b \\ c & d \end{bmatrix} \begin{pmatrix} x \\ y \end{pmatrix} \quad (4)$$

and therefore $$x'=ax+by \quad y'=cx+dy \quad (5)$$

This matrix operator can be decomposed into 4 simple matrices as follows:

$$\begin{bmatrix} a & b \\ c & d \end{bmatrix} = \begin{bmatrix} a & b \\ c & d \end{bmatrix}$$

$$= \left| \begin{pmatrix} \frac{b+c}{2} - \frac{b-c}{2} \end{pmatrix} \begin{pmatrix} \frac{a+d}{2} + \frac{a-d}{2} \end{pmatrix} \quad \begin{pmatrix} \frac{b+c}{2} + \frac{b-c}{2} \end{pmatrix} \\ \begin{pmatrix} \frac{b+c}{2} - \frac{b-c}{2} \end{pmatrix} \quad \begin{pmatrix} \frac{a+d}{2} - \frac{a-d}{2} \end{pmatrix} \right|$$

$$= \begin{bmatrix} a & b \\ c & d \end{bmatrix}$$

$$= \frac{a+d}{2}\begin{bmatrix} 1 & 0 \\ 0 & 1 \end{bmatrix} + \frac{a-d}{2}\begin{bmatrix} 1 & 0 \\ 0 & -1 \end{bmatrix} + \frac{b+c}{2}\begin{bmatrix} 0 & 1 \\ 1 & 0 \end{bmatrix} + \frac{b-c}{2}\begin{bmatrix} 0 & 1 \\ -1 & 0 \end{bmatrix}$$

Thus Eq. (4) may be written as:

$$\begin{pmatrix} x' \\ y' \end{pmatrix} = \left\{ \frac{a+d}{2}\begin{bmatrix} 1 & 0 \\ 0 & 1 \end{bmatrix} + \frac{a-d}{2}\begin{bmatrix} 1 & 0 \\ 0 & -1 \end{bmatrix} + \frac{b+c}{2}\begin{bmatrix} 0 & 1 \\ 1 & 0 \end{bmatrix} + \frac{b-c}{2}\begin{bmatrix} 0 & 1 \\ -1 & 0 \end{bmatrix} \right\} \begin{pmatrix} x \\ y \end{pmatrix}$$

or $$\begin{pmatrix} x' \\ y' \end{pmatrix} = \frac{a+d}{2}\begin{bmatrix} 1 & 0 \\ 0 & 1 \end{bmatrix}\begin{pmatrix} x \\ y \end{pmatrix} + \frac{a-d}{2}\begin{bmatrix} 1 & 0 \\ 0 & -1 \end{bmatrix}\begin{pmatrix} x \\ y \end{pmatrix} + \frac{b+c}{2}\begin{bmatrix} 0 & 1 \\ 1 & 0 \end{bmatrix}\begin{pmatrix} x \\ y \end{pmatrix} + \frac{b-c}{2}\begin{bmatrix} 0 & 1 \\ -1 & 0 \end{bmatrix}\begin{pmatrix} x \\ y \end{pmatrix}$$

The action of these 4 simple matrices may be interpreted as follows. The first matrix can be recognized as the identity matrix [I] and it can represent the expansion or contraction of space in a homogeneous way so that a square grid is transformed into second square grid that is bigger or smaller than the original grid. The second matrix can have the effect of turning a square grid into a rectangular one in that the quantity x(a−d)/2 is added to x position while y(a−d)/2 is subtracted from the y position. We have given the second simple matrix the symbol [+].

The third matrix can create a parallelogram effect in that the quantity y(b+d)/2 is added to the x position while x(b+d)/2 is added to they position. We have given the third simple matrix the symbol [X]. The fourth matrix can have the effect of turning the parallelogram into a quadrilateral as the quantity y(b−d)/2 is added to the x position while the quantity y(b−d)/2 is subtracted from they position. Following the general mathematical practice, the fourth simple matrix is given the symbol [J].

The four simple matrices [I], [+], [X] and [J] plus their negatives form a representation of the 4 element finite group called the dihedral group D4. This group may also be called the Refractive group, and can be useful in analysis of the propagation of sphero cylindrical wavefronts, as more fully explained an article by Charles Campbell entitled, "The refractive group", Optometry and Vision Science, 74 (6), 381-387, June 1997. Using these symbols, Eq. (4) may be written as:

$$\begin{pmatrix} x' \\ y' \end{pmatrix} = \left\{ \frac{a+d}{2}[I] + \frac{a-d}{2}[+] + \frac{b+c}{2}[X] + \frac{b-c}{2}[J] \right\} \begin{pmatrix} x \\ y \end{pmatrix}$$

In the type of distortion of light ray patterns in physical space which can be of interest here, for example distortion that arises from the propagation of rays of a sphero cylindrical wavefront, the coefficients b and c can be equal so that Eq. (4) takes the form of:

$$\begin{pmatrix} x' \\ y' \end{pmatrix} = \begin{bmatrix} a & b \\ b & d \end{bmatrix}\begin{pmatrix} x \\ y \end{pmatrix} \tag{4a}$$

and therefore $$x'=ax+by \quad y'=bx+dy \tag{5a}$$

When Eq. (4) this form, the coefficient of matrix [J] are generally zero and the coefficient of matrix [X] becomes b thus Eq. (4) may be written as:

$$\begin{pmatrix} x' \\ y' \end{pmatrix} = \left\{ \frac{a+d}{2}\begin{bmatrix} 1 & 0 \\ 0 & 1 \end{bmatrix} + \frac{a-d}{2}\begin{bmatrix} 1 & 0 \\ 0 & -1 \end{bmatrix} + b\begin{bmatrix} 0 & 1 \\ 1 & 0 \end{bmatrix} \right\} \begin{pmatrix} x \\ y \end{pmatrix}$$

or $$\begin{pmatrix} x' \\ y' \end{pmatrix} = \frac{a+d}{2}\begin{bmatrix} 1 & 0 \\ 0 & 1 \end{bmatrix}\begin{pmatrix} x \\ y \end{pmatrix} + \frac{a-d}{2}\begin{bmatrix} 1 & 0 \\ 0 & -1 \end{bmatrix}\begin{pmatrix} x \\ y \end{pmatrix} + b\begin{bmatrix} 0 & 1 \\ 1 & 0 \end{bmatrix}\begin{pmatrix} x \\ y \end{pmatrix}$$

and using the symbols for the simple matrices $$\begin{pmatrix} x' \\ y' \end{pmatrix} = \left\{ \frac{a+d}{2}[I] + \frac{a-d}{2}[+] + b[X] \right\} \begin{pmatrix} x \\ y \end{pmatrix}$$

and if b≠c $$\begin{pmatrix} x' \\ y' \end{pmatrix} = \left\{ \frac{a+d}{2}[I] + \frac{a-d}{2}[+] + \frac{b+c}{2}[X] + \frac{b-c}{2}[J] \right\} \begin{pmatrix} x \\ y \end{pmatrix} \tag{4b}$$

4.3 Fourier Transform of Distorted Arrays

Now we return to the effect on the Fourier transform caused by the third and fourth matrices. To assist in this investigation, a concept representing a grid array as a periodic function can be introduced. A periodic function $f(x,y)$ can have the property that when x and y are increased by amounts $np_x$ and $mp_y$ respectively so that $x'=x+np_x$ and $y'=y+mp_y$, $f(x,y)=f(x', y')=f(x+np_x, y+mp_y)$, where n and m are integers and $p_x$ and $p_y$ the periods for x and y respectively. Further, such functions may also be represented as a sum of delta functions as $$f(x, y) = \delta(x-np_x)\delta(y-mp_y) \tag{6}$$

wherein $\delta(x-np_x)=1$ if $x=np_x$ and is 0 otherwise $\delta(y-mp_y)=1$ if $=mp_y$ and is 0 otherwise Notice that since Eq. (6) is the product of two delta functions, both conditions can be satisfied where the expression is non-zero. This can insure that only locations on the grid corresponding to non-zero values of the delta functions give non-zero values.

Figure 11A:
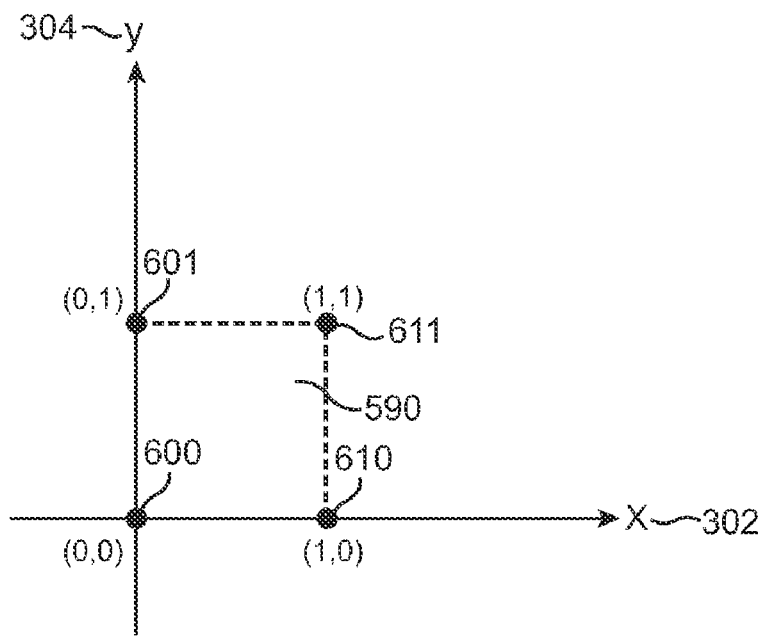
FIG. 11A illustrates positions of an initial location of a group of light rays as a unit cell.
Figure 11B:
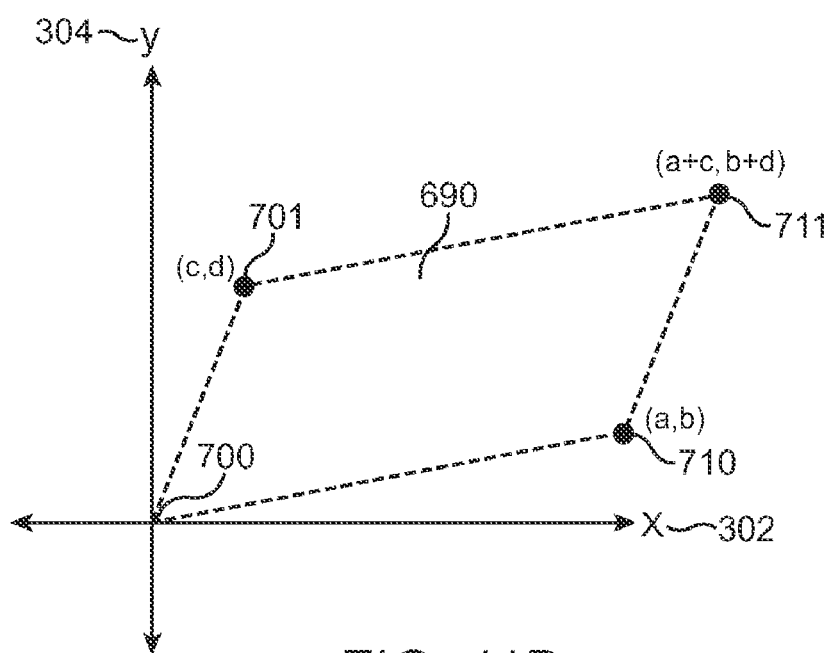
FIG. 11B illustrates positions of a group of light rays which have propagated from the initial location as in FIG. 11A to form a first cell of a skew periodic array of light rays.
Figure 11C:
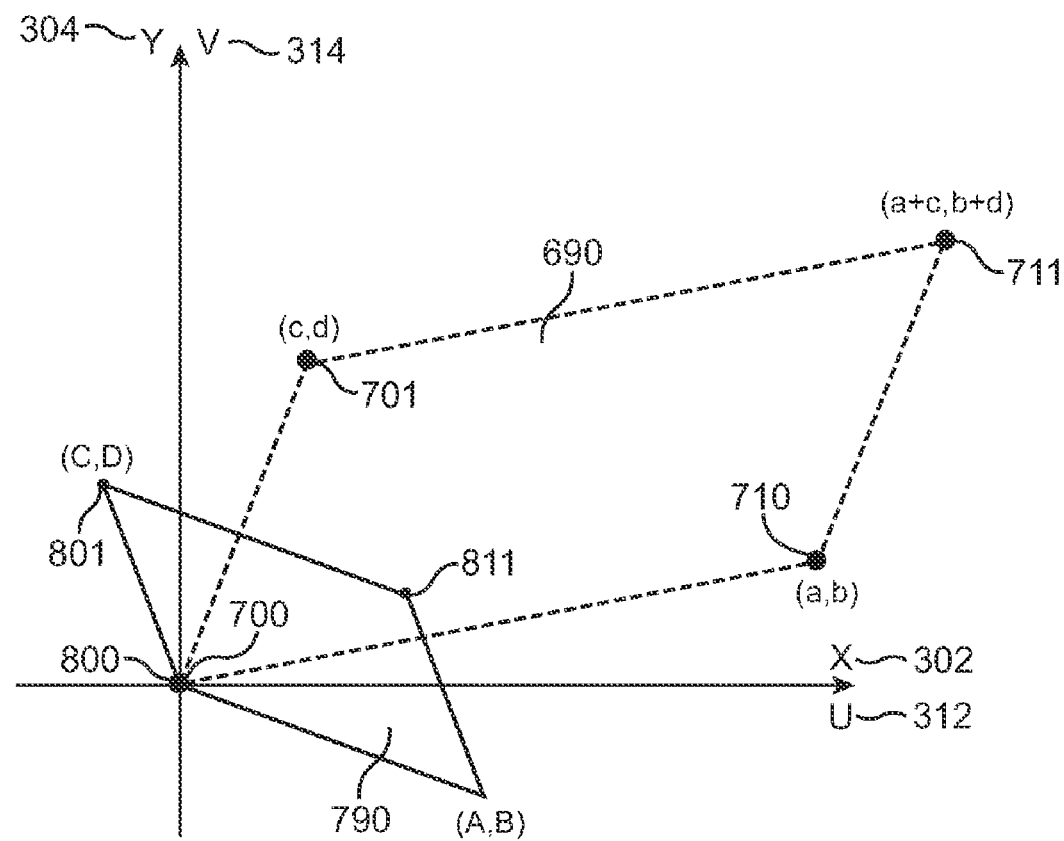
FIG. 11C illustrates a map in frequency space showing intensities of spatial frequencies which result from mapping a skew periodic array as in FIG. 11B to frequency space.

To turn this expression into one for a skew-periodic array, the x and y values in Eqs. (5) can be the index values m and n so that in place of $mp_x$ and $np_y$ the expressions (an+bm) and (cn+dm) are substituted and Eq, (6) becomes $f(x,y)=\delta(x-an-bm)\delta(y-cn-dm)$ This equation may now be used to see how this function maps into spatial frequency space. A grid that is infinite in extent and so represented by $$g(x, y) = \sum_{n=-\infty}^{\infty} \sum_{m=-\infty}^{\infty} \delta(x - na - mb)\delta(y - nc - md)$$

and has as its Fourier transform $$G(u, v) = \sum_{n=-28}^{\infty} \sum_{m=-\infty}^{\infty} \delta(u - nA - mB)\delta(v - nC - mD)$$

where
A, B, C and D are the transformation matrix coefficients in the spatial frequency space that specify the grid in that space and are functionally related to the similar coefficients a, b, c and d in the data space Referring now to FIGS. 11A-C, the functional relationship between coefficients a, b, c and d and coefficients A, B, C and D are illustrated. This relationship is illustrated, with simplifying modifications, in FIGS. 11A-C. First the x-y data space and unit cell are illustrated in FIG. 11A. The subsequently propagated skew array in data space is illustrated in FIG. 11B. Finally, the skew array is illustrated u-v spatial frequency space in FIG. 11C.

Referring to FIG. 11A, an initial unit cell 590 is illustrated. The unit cell is bounded at four corners 600, 601, 611 and 610. Each of four corners 600, 601, 611 and 610 corresponds to coordinate locations along X and Y coordinate references in physical data space of (0,0), (0,1), (1,1) and (1,0) respectively. Each side of the unit cell is 1 unit long and one corner is at the origin of the physical data coordinate system at coordinate reference (0,0).

Referring now to FIG. 11B, the initial unit cell is illustrated as transformed by a general transformation from the unit cell into the first cell of a skew-periodic array, referred to as the skew periodic unit cell 619. This transformation corresponds to the propagation of light rays as set forth above. The skew periodic cell is bounded at four corners 700, 701, 711 and 710. Each of four corners 700, 701, 711 and 710 corresponds to coordinate locations along X and Y coordinate references in physical data space of (0,0), (c,d), (a+c, b+d) and (a,b) respectively. Since the cell at the origin has been chosen as the initial cell the coordinates of the skew-periodic cell can take the simple form shown.

Referring now to FIG. 11C, the skew-periodic unit cell is illustrated in XY data space and a spatial frequency skew periodic unit cell 790 in UV spatial frequency space. In this illustration, the skew periodic array has been mapped from physical data space to transform space by a transform function, here frequency space by the Fourier transform. This transformation corresponds to the mapping of the skew periodic array into discrete spatial frequency values at discrete spatial frequency coordinate references. The spatial frequency skew periodic unit cell is bounded at four corners 800, 801, 811 and 810. Each of four corners 800, 801, 811 and 810 corresponds to coordinate locations along first and second coordinate references in transform space, here spatial frequency space along dimensions U and V. The coordinate reference locations of points 800, 801, 811 and 810 in frequency space are (0,0), (C,D), (A+C, B+D) and (A,B) respectively.

The length of the data skew-periodic unit cell side from the origin to point (a,b) can be expressed as $\sqrt{a^2+b^2}$. The length of spatial frequency skew—periodic unit cell from the origin to point (A,B) can be expressed as $\sqrt{A^2+B^2}$. Papuolis states that if the line from the origin to point (a,b) can be considered to be vector |ab⟩ and the line from the origin to point (A,B) can be considered to be vector |AB⟩ then the projection of |AB⟩ onto |ab⟩ is equal to N/|ab| where N corresponds to a number of rows of data as set forth above. This projection can then be expressed as:

$$\frac{\langle ab | AB \rangle}{\sqrt{a^2+b^2}} = \frac{(a,b)\binom{A}{B}}{\sqrt{a^2+b^2}} \qquad (7)$$

$$= \frac{aA+bB}{\sqrt{a^2+b^2}}$$

$$= \frac{N}{\sqrt{a^2+b^2}} aA + bB$$

$$= N$$

Likewise, the projection of vector |CD⟩ onto vector |cd⟩ is equal to M/|cd| where M corresponds to a number of columns of data, giving:

$$\frac{\langle cd | CD \rangle}{\sqrt{c^2+d^2}} = \frac{(c,d)\binom{C}{D}}{\sqrt{c^2+d^2}} \qquad (8)$$

$$= \frac{cC+dD}{\sqrt{c^2+d^2}}$$

$$= \frac{M}{\sqrt{c^2+d^2}} cC + dD$$

$$= M$$

In addition to the above conditions, the vector |ab⟩ can be perpendicular to vector |CD⟩ and |cd⟩ can be perpendicular to vector |AB⟩. This relationship can then be expressed as $$\langle ab | CD \rangle = (a,b)\binom{C}{D} = aC + bD = 0 \qquad (9)$$

$$aC = -bD$$

and $$\langle cd | AB \rangle = (c, d)\begin{pmatrix} A \\ B \end{pmatrix} = cA + dB = 0 \qquad (10)$$

$$cA = -dB$$

Eq. (9) can now be used in the form $$\frac{-aC}{D} = b$$

in Eq. (7) so that a may found in terms of the quantities A,B,C,D and N as $$aA - \frac{aC}{D}B = a\left(\frac{AD - BC}{D}\right) = N \qquad (11)$$

$$a = \frac{ND}{AD - BC}$$

Eq. (11) can now be used in $$\frac{-aC}{D} = b$$

to find the expression for b in terms of the quantities A,B,C,D and N as $$b = \frac{-NB}{AD - BC} \qquad (12)$$

A similar treatment using Eq. (10) in Eq. (8) gives $$\frac{-dB}{A}C + dD = d\left(\frac{AD - BC}{A}\right) = M \qquad (13)$$

$$d = \frac{NA}{AD - BC}$$

One reason for solving for a,b,c and d in terms of A,B,C and D is that the skew-periodic values for the spatial frequency grid can be found first. These spatial frequency values (A, B, C and D) can then be used to determine the values of the skew periodic array. Note that if coefficients c=b=0, i.e. the data grid pattern is not skew, Eqs. (12) and (13) reduce to the form of Eq. (3) for a rectangular grid, showing the Eqs. (12) and (13) have the correct action. In addition, if B=C=0 then by Eq. (12) b=c=0 and vice versa.

4.4 The Action of Sphero Cylindrical Non-Zero wavefront on a Shack-Hartmann Pattern.

Usually a Shack-Hartmann sensor consists of an array of lenslets arranged in a square grid with a given pitch (distance between lenslet centers) ppl. At some distance t, usually the focal length of the lenslet in the lenslet array, from the lenslet array is a CCD sensor whose pixels are spaced from one another by the pixel pitches ppx and ppy. Sometimes, but not always, ppx=ppy. In many embodiments, it can be assumed that the ray of the wavefront under measurement strikes the center of a lenslet, and hence is not deflected by the lenslet. Such rays represent the center of the subsequent spot pattern that all the rays passing through that lenslet forms on the CCD sensor. Thus a measurement of the center of a spot pattern can give information on the slope of the ray in the wavefront at the location of the center of the lenslet as the wavefront strikes the lenslet array. By using the known value of t, the angular deflection components of the wavefront passing through the lenslet at that point may be found by dividing the distance the ray has moved on the CCD array, in the x and in the y directions.

If the wavefront has a sphero cylindrical error and the values of this error are known, the deflection may be calculated using the following theory that employs concepts of the Refractive Group. Usually it is ophthalmic practice to specify a refractive error in terms of a sphere value S, a cylinder value C and a cylinder axis A. However embodiments of the invention decompose the error into the three elements of the refractice group, mean power error M, cross-cylinder at 90/180 degrees C.+ and cross-cylinder at 45/135 degrees C.x. The well known formulas to make this conversion are $$M=S+C/2$$

$$C+=C/2 \cos(2A)$$

$$Cx=C/2 \sin(2A)$$

The deflection $|\delta\rangle$ given to a ray by this error at location (x,y) can be given by $$|\delta\rangle = \begin{pmatrix} \delta x \\ \delta y \end{pmatrix} = \{-M[I] + C_+[+] + Cx[X]\}\begin{pmatrix} x \\ y \end{pmatrix}$$

where x and y are positions in the wavefront measured from the point where a ray is undeviated by the wavefront error. Examples of such positions are the locations (0,0), (0,1), (1,1) and (1,0) of the unit cell as set forth above.

To find the position of the ray after it travels a distance t, the following expression can be used $$\begin{pmatrix} x' \\ y' \end{pmatrix} = \begin{pmatrix} x \\ y \end{pmatrix} + t\begin{pmatrix} \delta x \\ \delta y \end{pmatrix} = \begin{pmatrix} x \\ y \end{pmatrix} + t\{-M[I] + C_+[+] + Cx[X]\}\begin{pmatrix} x \\ y \end{pmatrix} \qquad (14)$$

$$\begin{pmatrix} x' \\ y' \end{pmatrix} = \{(1 - tM)[I] + tC_+[+] + tCx[X]\}\begin{pmatrix} x \\ y \end{pmatrix}$$

Examples of such positions are the coordinates of the skew periodic array as set forth above. When the form of Eq. (14) is compared to that of Eq. (4b) it can be seen that they are quite similar. However, Eq. (4b) has a [J] term whereas Eq. (14) does not. Before directly using these facts to solve for the refractive component values using the skew-periodic coefficient for the data set several other things can be considered. For example, the units of x and y in Eq. (14) can be in units of length whereas x and y in Eq. (4b) can be expressed in pure numbers, the number of grid units in the x and y directions. In addition, the number of grid units in the x direction per unit length can be different than the number of grid units in the the y direction per unit length for the CCD used in the sensor system. Thus before the two equations are directly compared, the x and y coordinates of one equation can be converted to the coordinate system of the other.

This problem can be treated by considering the two points on the data grid closest to the origin and determining how they change position from the zero power case to the case of non-zero refractive error. The initial locations can have the coordinate values $$|spot1\rangle = \begin{pmatrix} ppl \\ 0 \end{pmatrix}$$

and $$|spot2\rangle = \begin{pmatrix} 0 \\ ppl \end{pmatrix}$$

where ppl is the lenslet array pitch in unit of length. When refractive error is added and Eq. (14) is used, the spot positions can be found to change to $$|spot1'\rangle = \{(1-tM)[I] + tC_+[+] + tCx[X]\}\begin{pmatrix} ppl \\ 0 \end{pmatrix} \quad (15)$$

$$= \begin{pmatrix} (1-tM+tC_+)ppl \\ (tCx)ppl \end{pmatrix}$$

$$|spot1'\rangle = ppl\begin{pmatrix} (1-tM+tC_+) \\ (tCx) \end{pmatrix}$$

$$|spot2'\rangle = \{(1-tM)[I] + tC_+[+] + tCx[X]\}\begin{pmatrix} 0 \\ ppl \end{pmatrix} \quad (16)$$

$$= \begin{pmatrix} (tCx)ppl \\ (1-tM-tC_+)ppl \end{pmatrix}$$

$$|spot2'\rangle = ppl\begin{pmatrix} (tCx) \\ (1-tM-tC_+) \end{pmatrix}$$

The initial spot positions expressed in pixel numbers, where the number pixels per unit length for x and y respectively are nx and ny, can be expressed as $$|spot1\rangle = \begin{pmatrix} nx(ppl) \\ 0 \end{pmatrix} = ppl\begin{pmatrix} nx \\ 0 \end{pmatrix}$$

$$|spot2\rangle = \begin{pmatrix} 0 \\ ny(ppl) \end{pmatrix} = ppl\begin{pmatrix} 0 \\ ny \end{pmatrix}$$

To find the spot locations in pixels when refractive error is present, Eq. (4b) can be used to give $$|spot1'\rangle = ppl\left\{\frac{a+d}{2}[I] + \frac{a-d}{2}[+] + \frac{b+c}{2}[X] + \frac{b-c}{2}[J]\right\}\begin{pmatrix} nx \\ 0 \end{pmatrix}$$

$$= ppl\begin{pmatrix} a(nx) \\ c(nx) \end{pmatrix}$$

$$|spot2'\rangle = ppl\left\{\frac{a+d}{2}[I] + \frac{a-d}{2}[+] + \frac{b+c}{2}[X] + \frac{b-c}{2}[J]\right\}\begin{pmatrix} 0 \\ ny \end{pmatrix}$$

$$= ppl\begin{pmatrix} b(ny) \\ d(ny) \end{pmatrix}$$

So that these pixel values may be expressed in length values, the x components can be divided by nx and they components are divided by ny. This division can convert the above expressions to $$|spot1'\rangle = ppl\begin{pmatrix} a \\ c(nx)/ny \end{pmatrix} \quad (17)$$

$$|spot2'\rangle = ppl\begin{pmatrix} b(ny)/nx \\ d \end{pmatrix} \quad (18)$$

Now Eq. (15) may be compared directly with Eq. (17) with the result that $$ppl\begin{pmatrix} a \\ c(nx)/ny \end{pmatrix} = ppl\begin{pmatrix} (1-tM+tC_+) \\ (tCx) \end{pmatrix}$$

Since the components can equal one another $$a = 1 - tM + tC_+$$

$$\frac{c(nx)}{ny} = tCx$$

Next, comparing Eq. (16) with Eq. (18)

$$ppl\begin{pmatrix} b(ny)/nx \\ d \end{pmatrix} = ppl\begin{pmatrix} (tCx) \\ (1-tM-tC_+) \end{pmatrix}$$

Since the components can equal one another $$d = 1 - tM - tC_+$$

$$\frac{b(ny)}{nx} = tCx$$

These four equations are now combined as follows to solve for the refractive error values.

$$\frac{a+d}{2} = 1 - tM; \, m = \frac{1}{t} - \frac{a+d}{2t} \quad (19)$$

$$\frac{a-d}{2} = tC_+; \, C_+ = \frac{a-d}{2t} \quad (20)$$

$$\frac{b(ny)/nx + c(nx)/ny}{2} = tCx; \, Cx = \frac{b(ny)/nx + c(nx)/ny}{2t} \quad (21)$$

Thus if the skew-periodic coefficients, a, b, c and d are found and t is known, the refractive error values may be immediately be calculated using Eqs. (19), (20) and (21).

In alternate embodiments, wavefront elevation maps can be calculated using the coordinate locations of the signals in transform space as set forth above. For example, a second order wavefront elevation map can be calculated using the coefficients corresponding to sphere, cylinder and axis. Such coefficients can generally describe a sphero cylindrical surface. More complex wavefronts can be calculated by combining several sphero cylindrical surfaces.

Figure 12A:
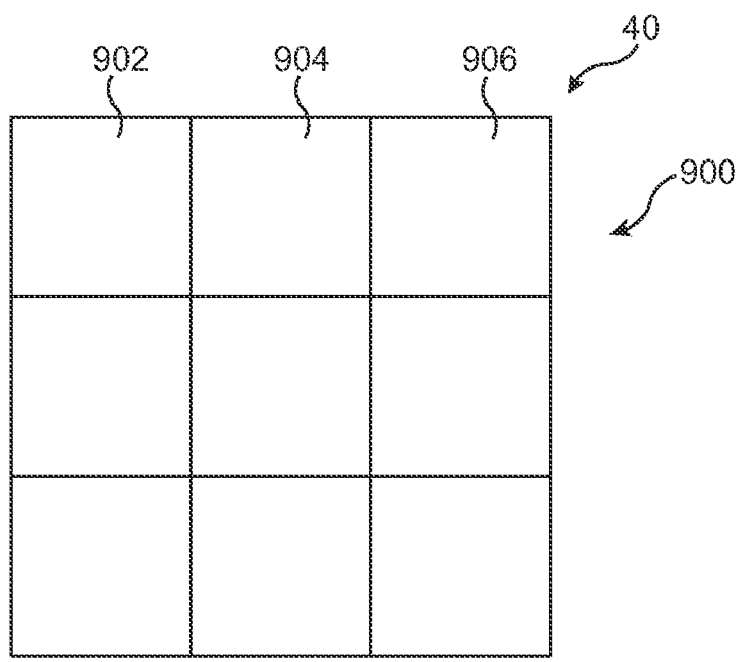
FIGS. 12A and 12B illustrate techniques for determining wavefront elevation maps.
Figure 12B:
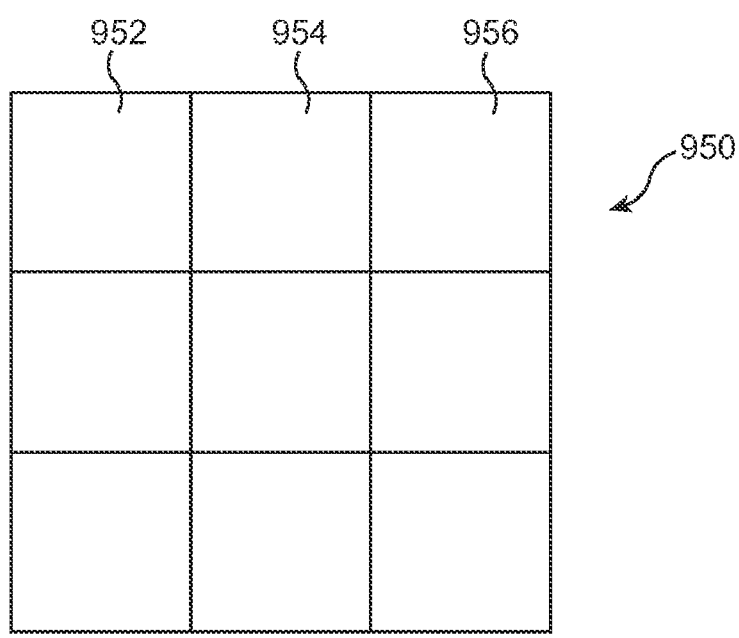

Referring now to FIGS. 12A and 12B, techniques for solving for wavefront elevation maps are illustrated in accordance with embodiments. An array of data 900 from detector 40 can be subdivided into smaller portions corresponding to smaller areas such as portions 902, 904, and 906. Each portion of the data corresponds to a portion of the optical surface. The technique of finding the second order sphero cylindrical wavefront as set forth above is implemented on each of the portions of the data, in many embodiments without finding a location of individual spots of light in the pattern. Localized sphero cylindrical surfaces such as localized sphero cylindrical surfaces 952, 954 and 956 are determined. Each localized sphero cylindrical surface corresponds to a portion of the optical surface. As each portion of the optical surface can be described by the localized sphero cylindrical surface, an entire optical surface 950 can be determined by combining the localized sphero cylindrical surfaces corresponding to each portion of the optical surface. Techniques such as finite element analysis and cubic spline fitting can be used to combine the localized sphero cylindrical surfaces and to provide a smooth wavefront elevation map over the entire optical surface.

4.5 Review of the Complete Method

The techniques of embodiments as described above can be summarized as follows. A measurement can be taken with a wavefront sensor to produce a spot pattern on a detector. The measured Shack-Hartmann spot pattern can be mapped to transform space with a FFT. After shifting the spatial frequency array so that the zero frequency is at the center, signals in transform space are analyzed. Specifically, the locations of the first order spatial frequency intensity peaks in transform space can be found. The coordinate reference locations of the mapped features in transform space can give the characteristic skew-periodic coefficients of the spatial frequency array, A, B, C and D. These characteristics derived from signals in transform space can be mapped back to physical space to characterize the optical surface and in particular provide a wavefront elevation map of the optical surface in physical space. For example, these characteristic spatial frequency coefficients permit determination of the pure sphero cylindrical error directly without finding the location of individual spots of light in the pattern. Using Eqs. (10), (11), (12) and (13), data space skew-coefficients a, b, c and d can be calculated from the characteristic spatial frequency components. These coefficients can be used with the values for nx, ny and t in the Eqs. (19), (20) and (21) to find the refractive components, M, C+ and Cx. The refractive components can be used to calculate a wavefront error map of the optical surface as described above.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A method of measuring an optical surface of a tissue system, the method comprising:
   forming a spatial distribution pattern on a detector by focusing a light energy propagating from the tissue system through several lenslets of a lenslet array onto the detector so that the pattern includes several spots of light energy;
   mapping the pattern to a transform array by transforming the pattern with a transform function so that the array comprises values corresponding to locations distributed in a spatial frequency space, each of the values of the array corresponding to an associated local intensity, in the frequency space of the several spots of the pattern;
   identifying a shape characteristic of the optical surface from a selected value, wherein the selected value is selected from the values of the transform array and corresponds to an associated local intensity, at the corresponding location in the frequency space, of the several spots; and
   selecting the selected value in response to identifying the selected value as a peak value from within the array.

2. The method of claim 1 wherein:
   the pattern comprises a two dimensional spatial light intensity distribution pattern;
   the array comprises a two dimensional array having values corresponding to a first coordinate reference along a first dimension in a transform space and a second coordinate reference along a second dimension in the transform space; and
   the characteristic corresponds to a first coordinate location along the first dimension and a second coordinate location along the second dimension.

3. The method of claim 2 further comprising identifying a second characteristic from the array, the second characteristic corresponding to a third coordinate reference along the first dimension and a fourth coordinate reference along the second dimension.

4. The method of claim 1, wherein the shape characteristic comprises a spherocylindrical power of the surface.

5. The method of claim 1, wherein the shape characteristic comprises a high-order aberration of the surface.

6. A system for determining an optical aberration characteristic of a surface of a tissue system, the system comprising:
   an optical system having an optical path and a lenslet array, the lenslet array including several lenslets and configured for forming several spots corresponding, to the several lenslets;
   a detector disposed along the optical path and configured for measuring a spatial light distribution energy pattern focused by the lenselet array, the pattern including the several spots;
   a processor coupled to the detector and configured to map the pattern to a signal in a transform space and determine the characteristic from the signal, wherein the processor is configured to map the pattern to an array having values corresponding to locations distributed in a frequency space, each of the values of the array corresponding to an associated local frequency intensity of the several spots of the pattern, wherein the processor is configured to determine the characteristic from a selected value from among the values of the transform array, the selected value corresponding to an associated local frequency intensity, in the frequency space, of the several spots, and wherein the processor is further configured to select the value such that the value comprises a peak value from within the array.

7. The system of claim 6, wherein the optical system is configured so that the pattern comprises a two dimensional spatial light intensity distribution pattern and wherein the processor is configured so that the array comprises a two dimensional array having values corresponding to a first coordinate reference along a first dimension in the transform space and a second coordinate reference along a second dimension in the transform space and wherein the characteristic corresponds to a first coordinate location along the first dimension and a second coordinate location along the second dimension, and wherein the processor is configured to identify a second characteristic from the transform array, the second characteristic corresponding to third coordinate reference along the first dimension and a fourth coordinate reference along the second dimension.

8. The system of claim 6, wherein the shape characteristic comprises a spherocylindrical power of the surface.

9. The system of claim 6, wherein the shape characteristic comprises a high-order aberration of the surface.

* * * * *